(12) United States Patent
Moser et al.

(10) Patent No.: US 10,344,316 B2
(45) Date of Patent: Jul. 9, 2019

(54) METHODS FOR DISTINGUISHING AND IDENTIFYING PLANT VARIETIES

(71) Applicant: SYNGENTA PARTICIPATIONS AG, Basel (CH)

(72) Inventors: Tricia C. Moser, Durham, NC (US); Rene Quadt, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 324 days.

(21) Appl. No.: 15/384,472

(22) Filed: Dec. 20, 2016

(65) Prior Publication Data

US 2017/0101663 A1    Apr. 13, 2017

Related U.S. Application Data

(63) Continuation of application No. 13/577,717, filed as application No. PCT/US2011/025671 on Feb. 22, 2011, now abandoned.

(60) Provisional application No. 61/306,764, filed on Feb. 22, 2010.

(51) Int. Cl.
*C12Q 1/40* (2006.01)
*C12N 9/32* (2006.01)
(52) U.S. Cl.
CPC ............. *C12Q 1/40* (2013.01); *C12N 9/2422* (2013.01)

(58) Field of Classification Search
None
See application file for complete search history.

(56) References Cited

U.S. PATENT DOCUMENTS

2006/0014265 A1    1/2006   Ferrari et al.
2006/0294620 A1    12/2006  Gray et al.
2008/0319927 A1    12/2008  Dallmier et al.

OTHER PUBLICATIONS

Johnston et al., Journal of Food Biochemistry, 1998, vol. 22, pp. 301-319.
Collado and Corke, J. Agric. Food Chem., 1998, 47, pp. 832-835.

*Primary Examiner* — Anand U Desai
(74) *Attorney, Agent, or Firm* — Karen A. Magri

(57) ABSTRACT

Methods are disclosed for distinguishing and identifying plants by measuring partial hydrolysis of polysaccharides on account of polysaccharide-hydrolyzing enzyme activity at pre-determined incubation times and temperatures. Methods also are disclosed for identifying the source organism of a heterologous polysaccharide-hydrolyzing enzyme in a plant by measuring partial hydrolysis of polysaccharides on account of polysaccharide-hydrolyzing enzyme activity at pre-determined incubation times and temperatures. The reaction mixture has unique chemical and physical properties that can be used to construct viscosity curves for measuring polysaccharide-hydrolyzing enzyme activity. The viscosity curves can be compared among plants to distinguish or identify the plants from one another. Likewise, viscosity curves can be compared among source organisms to identify the source organism of the heterologous polysaccharide-hydrolyzing enzyme in the plant.

14 Claims, 10 Drawing Sheets

METHODS FOR DISTINGUISHING AND IDENTIFYING PLANT VARIETIES

CROSS REFERENCE TO RELATED APPLICATIONS

This application is a continuation of U.S. application Ser. No. 13/577,717, filed Aug. 8, 2012, which is a 371 of International Application No. PCT/US2011/025671, filed Feb. 22, 2011, which claims priority to U.S. Provisional Application No. 61/306,764, filed Feb. 22, 2010.

FIELD OF THE INVENTION

The invention relates generally to methods of distinguishing and identifying plant varieties, and more particularly to distinguishing and identifying plant varieties by observing, on account of a polysaccharide-hydrolyzing enzyme, changes in chemical and physical properties of a polysaccharide-containing sample at a pre-determined temperature over a short, yet pre-determined, time.

BACKGROUND OF THE INVENTION

Traditionally, plant varieties have been distinguished or identified based on phenotypic (i.e., morphologic) characteristics. See, e.g., Wrigley, pp. 17-41 In: *Modern Methods of Plant Analysis*, Vol. 14 (Linskens & Jackson eds., Springer Verlag 1992). Distinguishing or identifying plant varieties by phenotypic characteristics, however, can be difficult when applied to inbred or transgenic plants, which may not display robust phenotypic variation among one another.

More recently, methods of distinguishing or identifying plant varieties have relied on detecting molecular markers (e.g., protein gel electrophoresis and PCR) and gene expression profiling. See, e.g., Ancillo et al. (2007) *J. Exp. Bot.* 58:1927-1933; Cooke (1995) *J. Chromatogr.* 698:281-299; de Riek et al. (2007) *Crop Sci.* 47:1964-1974; and Lee et al. (2005) *Electrophoresis* 17:261-265; as well as U.S. Pat. No. 5,948,650. Likewise, visible-near infrared spectroscopy or matrix-assisted laser desorption/ionization time-of-flight mass spectrometry (MALDI-TOFMS) can be used to distinguish or identify plant varieties. See, e.g., Bloch et al. (1999) *Rapid Commun. Mass Spectrom.* 13:1535-1539; Chen et al. (2007) *Spectrochim. Acta A* 66:568-574; Perez et al. (2001) *J. Food Sci.* 66:323-327; Wang & Paliwal (2006) *Trans. ASABE* 49:1607-1612; Xie et al. (2007) *J. Food Eng.* 82:395-401; and Xu et al. (2009) *J. Zhejiang Univ. Sci. B* 10:126-132. These methods, however, can be expensive and/or can be time-consuming.

An ability to distinguish and identify plant varieties, as well as an ability to identify a source organism for a heterologous polysaccharide-hydrolyzing enzyme in a plant, is important to the seed and related industries. As such, there is a need for inexpensive and rapid methods of distinguishing and identifying plant varieties and source organisms of heterologous polysaccharide-hydrolyzing enzymes that can be found in plants.

BRIEF SUMMARY OF THE INVENTION

Methods are provided for distinguishing and identifying plant varieties. Likewise, the methods can be used to determine the source organism of a heterologous polysaccharide-hydrolyzing enzyme in a plant. The methods involve measuring changes in chemical and physical properties of a plant sample, such as viscosity, which can be affected by a polysaccharide-hydrolyzing enzyme. The viscosity changes can result from activity of the polysaccharide-hydrolyzing enzyme in degrading polysaccharides in the plant sample. The methods involve measuring viscosity of the plant sample at a pre-determined temperature over a short, yet pre-determined, time. These methods provide a rapid and reliable assay.

Specifically, the methods involve measuring viscosity changes in a plant sample resulting from activity of a polysaccharide-hydrolyzing enzyme in degrading a polysaccharide. The viscosity changes can be used to obtain a viscosity curve that can be compared to a curve obtained from another plant to distinguish two plants from one another if they are of different varieties. Alternatively, the viscosity changes can be used to obtain a viscosity curve that can be compared to known viscosity curves from known plant varieties to identify the plant variety. Likewise, the viscosity changes can be used to obtain a viscosity curve that can be compared to viscosity curves from known polysaccharide-hydrolyzing enzymes to identify the source organism of a heterologous polysaccharide-hydrolyzing enzyme in the plant.

The methods described herein may be useful in a variety of applications. For example, the methods can be used to distinguish one or more plants from one another or to identify a plant variety present in samples at grain elevators and ethanol plants prior to storage or processing. Likewise, the methods can be used to identify the source organism of a heterologous polysaccharide-hydrolyzing enzyme in a plant. At ethanol plants, ethanol manufacturers use α-amylase to hydrolyze corn starch into sugars, which are later fermented to produce ethanol. Thus, ethanol manufactures can identify the plant or plants present or can identify the polysaccharide-hydrolyzing enzyme present in the plant material prior to producing ethanol.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the embodiments recited herein for interpreting the scope of the invention.

The following embodiments are encompassed by the present invention.

1. A method of distinguishing a first plant from a second plant, the method comprising the steps of:
    a. heating a solution of a milled plant part from the first plant that comprises a polysaccharide-hydrolyzing enzyme and polysaccharide substrate to a temperature above a gelatinization temperature of the polysaccharide substrate;
    b. measuring viscosity changes of the solution for about 10 seconds to about 2 minutes;
    c. obtaining a viscosity curve for the first plant; and
    d. comparing the viscosity curve from the first plant to a viscosity curve obtained in the same manner from the second plant, wherein differences in the slopes of the viscosity curves distinguish the first plant from the second plant.

2. The method of embodiment 1, wherein the temperature is between about 60° C. to about 100° C.

3. The method of embodiment 1, wherein the temperature is at least 80° C.

4. The method of embodiment 1, wherein the temperature is about 95° C.

5. The method of embodiment 1, wherein viscosity changes are measured from about 10 seconds to about 60 seconds.

6. The method of embodiment 1, wherein viscosity changes are measured at about 60 seconds.

7. The method of embodiment 1, wherein viscosity changes are measured at about 45 seconds.

8. The method of embodiment 1, wherein viscosity changes are measured at about 30 seconds.

9. The method of embodiment 1, wherein viscosity changes are measured at about 10 seconds.

10. The method of embodiment 1, wherein the polysaccharide substrate is starch.

11. The method of embodiment 1, wherein the polysaccharide-hydrolyzing enzyme is amylase.

12. The method of embodiment 1, wherein the polysaccharide-hydrolyzing enzyme is a thermotolerant amylase.

13. The method of embodiment 12, wherein the thermotolerant amylase is 797GL3 or D45.

14. The method of embodiment 1, wherein the plant part is from maize.

15. The method of embodiment 14, wherein the maize is a maize seed.

16. The method of embodiment 1, wherein step a is performed for about 1 minute to about 3 minutes.

17. A method of identifying a plant, the method comprising the steps of:
   a. heating a solution of a milled plant part comprising a polysaccharide-hydrolyzing enzyme and polysaccharide substrate to a temperature above a gelatinization temperature of the polysaccharide substrate, wherein the milled plant part is from a plant to be identified;
   b. measuring viscosity changes of the solution for about 10 seconds to about 2 minutes;
   c. obtaining a viscosity curve for the plant; and
   d. comparing the viscosity curve from the plant to known viscosity curves obtained in the same manner from known plant varieties, wherein substantial similarities in the slopes of the viscosity curves can be used to identify the plant.

18. The method of embodiment 17, wherein the temperature is between about 60° C. to about 100° C.

19. The method of embodiment 17, wherein the temperature is at least 80° C.

20. The method of embodiment 17, wherein the temperature is about 95° C.

21. The method of embodiment 17, wherein viscosity changes are measured from about 10 seconds to about 60 seconds.

22. The method of embodiment 17, wherein viscosity changes are measured at about 60 seconds.

23. The method of embodiment 17, wherein viscosity changes are measured at about 45 seconds.

24. The method of embodiment 17, wherein viscosity changes are measured at about 30 seconds.

25. The method of embodiment 17, wherein viscosity changes are measured at about 10 seconds.

26. The method of embodiment 17, wherein the polysaccharide substrate is starch.

27. The method of embodiment 17, wherein the polysaccharide-hydrolyzing enzyme is amylase.

28. The method of embodiment 17, wherein the polysaccharide-hydrolyzing enzyme is a thermotolerant amylase.

29. The method of embodiment 28, wherein the thermotolerant amylase is 797GL3 or D45.

30. The method of embodiment 17, wherein the plant part is from maize.

31. The method of embodiment 30, wherein the maize is a maize seed.

32. The method of embodiment 17, wherein step a is performed for about 1 minute to about 3 minutes.

33. A method of identifying a source organism of a heterologous polysaccharide-hydrolyzing enzyme in a plant, the method comprising the steps of:
   a. heating a solution of a milled plant part comprising a heterologous polysaccharide-hydrolyzing enzyme and polysaccharide substrate to a temperature above a gelatinization temperature of the polysaccharide substrate, wherein the milled plant part is from a plant to be identified;
   b. measuring viscosity changes of the solution for about 10 seconds to about 2 minutes;
   c. obtaining a viscosity curve for the plant; and
   d. comparing the viscosity curve from the plant to known viscosity curves obtained in the same manner from known polysaccharide-hydrolyzing enzymes, wherein substantial similarities in the slopes of the viscosity curves can be used to identify the source organism of the heterologous polysaccharide-hydrolyzing enzyme in the plant.

34. The method of embodiment 33, wherein the temperature is between about 60° C. to about 100° C.

35. The method of embodiment 33, wherein the temperature is at least 80° C.

36. The method of embodiment 33, wherein the temperature is about 95° C.

37. The method of embodiment 33, wherein viscosity changes are measured from about 10 seconds to about 60 seconds.

38. The method of embodiment 33, wherein viscosity changes are measured at about 60 seconds.

39. The method of embodiment 33, wherein viscosity changes are measured at about 45 seconds.

40. The method of embodiment 33, wherein viscosity changes are measured at about 30 seconds.

41. The method of embodiment 33, wherein viscosity changes are measured at about 10 seconds.

42. The method of embodiment 33, wherein the polysaccharide substrate is starch.

43. The method of embodiment 33, wherein the polysaccharide-hydrolyzing enzyme is amylase.

44. The method of embodiment 33, wherein the polysaccharide-hydrolyzing enzyme is a thermotolerant amylase.

45. The method of embodiment 44, wherein the thermotolerant amylase is 797GL3 or D45.

46. The method of embodiment 33, wherein the plant part is from maize.

47. The method of embodiment 46, wherein the maize is a maize seed.

48. The method of embodiment 33, wherein step a is performed for about 1 minute to about 3 minutes.

49. A method of identifying a maize hybrid comprising a polysaccharide-hydrolyzing enzyme, the method comprising the steps of:
   a. milling said maize hybrid seed to create a flour;
   b. adding water to a) wherein the addition of water results in a 10-50% dry solids corn slurry
   c. heating the corn slurry of b) to a temperature above a gelatinization temperature of the polysaccharide substrate;

d. mixing the corn slurry of step c)
e. measuring viscosity of d) at a time point between 10 to 100 seconds;
f. measuring the activity of said polysaccharide-hydrolyzing enzyme;
g. extrapolating the viscosity data and activity data of e) and f) onto a database of standard curves wherein the database of standard curves contains standard curved of known maize hybrids and the standard curve is plotted in relation to polysaccharide-hydrolyzing enzyme and viscosity at a time point between 10 to 100 seconds; and
h. comparing the standard curve of the unidentified maize hybrid to the standard curve of the identified maize hybrid, wherein differences in the slopes of the standard curves can be used to identify said maize hybrid.

50. The method of embodiment 49, wherein d) is carried out between about 60° C. to about 100° C.

51. The method of embodiment 49, wherein d) is carried out at about at least 80° C.

52. The method of embodiment 49, d) is carried out at about at least 95° C.

53. The method of embodiment 49, wherein viscosity changes in e) are measured from about 10 seconds to about 80 seconds.

54. The method of embodiment 49, wherein viscosity changes in e) are measured at about 74 seconds.

55. The method of embodiment 49, wherein the polysaccharide substrate is starch.

56. The method of embodiment 49, wherein the polysaccharide-hydrolyzing enzyme is amylase.

57. The method of embodiment 49, wherein the polysaccharide-hydrolyzing enzyme is a thermotolerant amylase.

58. The method of embodiment 49, wherein the thermotolerant amylase is 797GL3 or D45.

59. The method of embodiment 49, wherein the activity of said polysaccharide-hydrolyzing enzyme is measured in Units per gram of flour.

60. The method of embodiment 49, wherein identification of said maize hybrid can be performed within about 2 minutes to about 60 minutes.

61. A method of distinguishing a first maize plant from a second maize plant, the method comprising the steps of:
a. milling seed of said first maize hybrid plant to create a flour;
b. adding water to a) wherein the addition of water results in a 10-50% dry solids corn slurry;
c. heating the corn slurry of b) to a temperature above a gelatinization temperature in the presence of a thermotolerant amylase;
d. mixing the corn slurry of step c)
e. measuring viscosity of d) at a time point between 10 to 100 seconds;
f. measuring the activity of said thermotolerant amylase;
g. obtaining a standard curve for the first maize plant; and
h. comparing the standard curve from the first maize plant to a standard curve obtained in the same manner for the second maize plant, wherein differences in the slopes of the viscosity curves distinguish the first plant from the second plant.

62. The method of embodiment 61, wherein the standard curves are plotted in relation to thermotolerant amylase activity and viscosity at a time point between 10 to 100 seconds.

63. A method of distinguishing a first maize plant from a second maize plant, the method comprising the steps of:
a. milling seed of said first maize hybrid plant to create a flour;
b. adding water to a) wherein the addition of water results in a 10-50% dry solids corn slurry;
c. heating the corn slurry of b) to a temperature above a gelatinization temperature in the presence of a thermotolerant amylase;
d. mixing the corn slurry of step c)
e. measuring viscosity of d) at a time point between 10 to 100 seconds;
f. measuring the glucose level of said d) at a time point between 10 to 100 seconds wherein said glucose level can be correlated to thermotolerant amylase activity;
g. obtaining a standard curve for the first maize plant; and
h. comparing the standard curve from the first maize plant to a standard curve obtained in the same manner for the second maize plant, wherein differences in the slopes of the viscosity curves distinguish the first plant from the second plant.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

Figure 1:
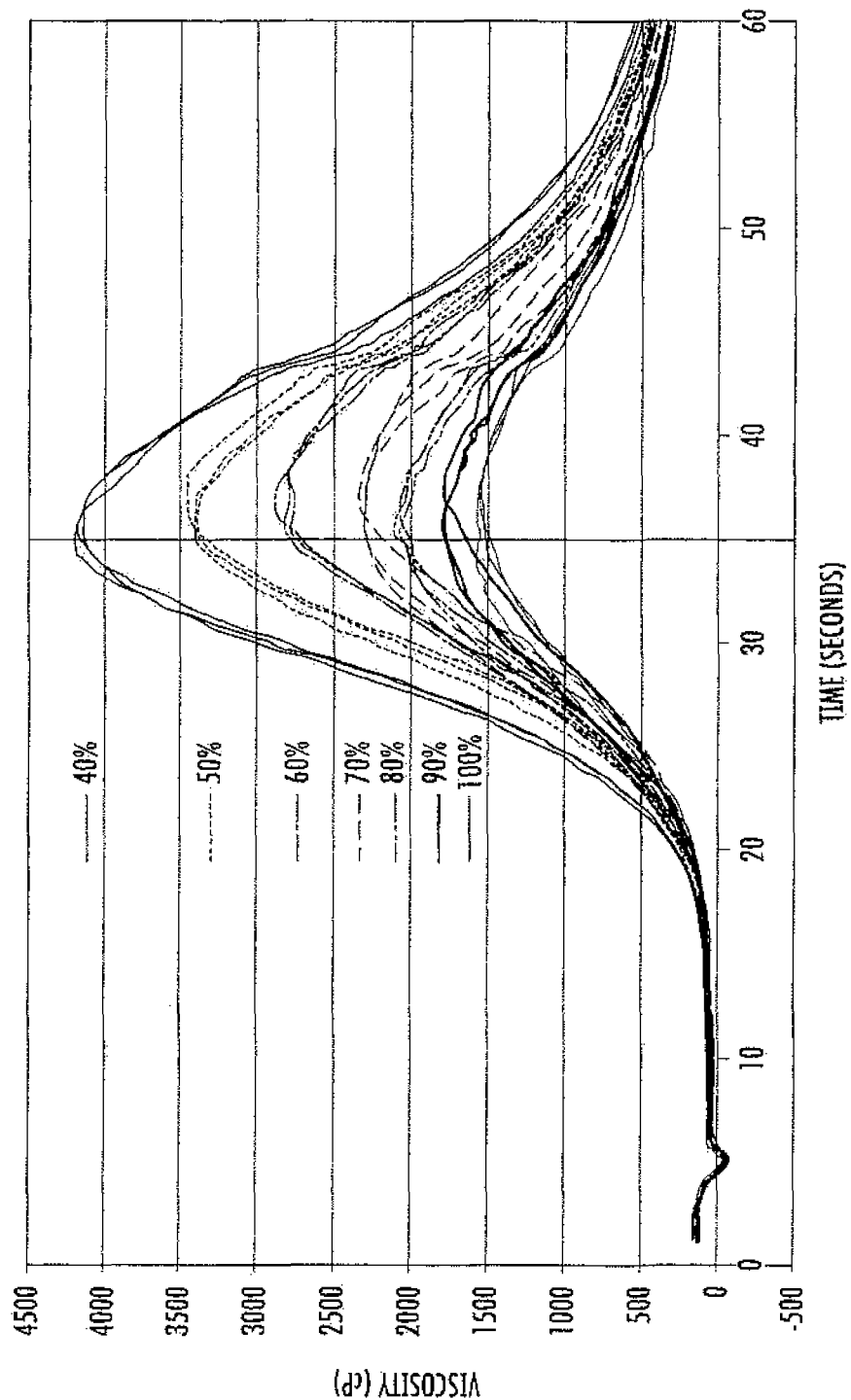
FIG. 1 shows measured viscosity of various thermotolerant amylase admix levels (40%, 50%, 60%, 70%, 80%, 90% and 100%) during a temperature ramp of 80° C. to 95° C. over 60 seconds.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

The present invention relates to methods of distinguishing and identifying plants from one another by measuring viscosity changes on account of polysaccharide-hydrolyzing enzyme activity in a sample from a plant having a polysaccharide-hydrolyzing enzyme, and comparing a viscosity curve from the sample to viscosity curves from another plant or to viscosity curves from known plants to distinguish or identify the plant, respectively. The present invention also relates to methods of identifying the source organism of a heterologous polysaccharide-hydrolyzing enzyme in a plant by measuring viscosity changes on account of polysaccharide-hydrolyzing enzyme activity in a sample from the plant having the heterologous polysaccharide-hydrolyzing enzyme, and comparing a viscosity curve from the sample to viscosity curves from known polysaccharide-hydrolyzing enzymes to identify the source organism of the heterologous polysaccharide-hydrolyzing enzyme in the plant. The methods involve measuring a viscosity change in the sample on account of the activity of a polysaccharide-hydrolyzing enzyme. The viscosity change results from the polysaccharide-hydrolyzing enzyme degrading polysaccharides or complex carbohydrates in the sample and can be correlated to the enzymatic activity of the polysaccharide-hydrolyzing enzyme from another plant or from known organisms or plants.

As used herein, "source organism" means an organism from which a polysaccharide-hydrolyzing enzyme was isolated and introduced into a plant not natively having that polysaccharide-hydrolyzing enzyme. Examples of source organisms for polysaccharide-hydrolyzing enzymes can be any prokaryote or eukaryote having the polysaccharide-hydrolyzing enzyme of interest, such as bacteria, especially thermophilic bacteria. The source organism also can be another plant.

As used herein, "plant having a heterologous polysaccharide-hydrolyzing enzyme" and the like means a plant having introduced into its genome a nucleotide sequence encoding a polysaccharide-hydrolyzing enzyme not native to the plant. As such, the nucleotide sequence can originate from a foreign organism (i.e., source organism), or, if from the plant, is substantially modified from its native form in composition and/or genomic locus by deliberate human intervention. Examples of such plants include, but are not limited to, transgenic plants or progeny thereof having integrated into their genome a nucleotide sequence encoding the heterologous polysaccharide-hydrolyzing enzyme of interest. Also included are plants obtained either by pollination with the same transformed strain or by cross-pollination with a different strain, but nonetheless have the heterologous polysaccharide-hydrolyzing enzyme of interest.

As used herein, the terms "Viscosity curve" and "standard curves" are used interchangeably to define a curve that is obtained by plotting viscosity readings obtained at a specific time point with activity of a polysaccharide-hydrolyzing enzyme (enzyme activity). This curve may contain either a single data point each for viscosity and enzyme activity, or in more preferred embodiments at least two data points each for viscosity and enzyme activity wherein enzyme activity is taken for two different enzyme concentrations (e.g. 25% admix and 75% admix), and in most preferred embodiments at least three data points each for viscosity and enzyme activity wherein enzyme activity is taken for at least three different enzyme concentrations. In some embodiments enzyme activity is measured in Units of enzyme per gram of substance.

The methods described herein therefore subject a polysaccharide to hydrolysis for a short, yet pre-determined, time and at a pre-determined temperature, resulting in partial hydrolysis of the polysaccharide. The reaction mixture and products from the partial hydrolysis have several unique properties. Such properties include, but are not limited to, the chemical products generated from the hydrolysis and the physical properties of the reaction mixture as the hydrolysis progresses. For example, the reaction mixture from starch hydrolysis is viscous, has soluble polysaccharide fragments (long chain), and has malto-oligosaccharides (short chain). Thus, these observable chemical and physical properties can be detected, estimated, measured or quantified to provide an activity or concentration for various polysaccharide-hydrolyzing enzymes. The methods described herein take advantage of these chemical and physical properties.

Overview

In one embodiment, the present invention relates to methods of distinguishing a first plant from a second plant by comparing viscosity curves based on the activity of a polysaccharide-hydrolyzing enzyme present in the plants. The methods involve measuring viscosity changes in a solution obtained from the first plant having a polysaccharide-hydrolyzing enzyme and an amount of polysaccharide. The solution can be at a temperature above a gelatinization temperature for the polysaccharide, and the viscosity changes can be measured for about ten seconds to about two minutes, such that a change in viscosity is indicative of the activity of the polysaccharide-hydrolyzing enzyme. The viscosity changes can be used to construct a viscosity curve for the first plant, which then can be compared to a viscosity curve obtained under similar assay conditions from the second plant. Differences between the slopes of the curves can be used to distinguish the first plant from the second plant. In the same manner, plants can be identified by comparing the viscosity curve for the plant with viscosity curves from known plants.

As used herein, "measuring" means not only observing the presence of the polysaccharide-hydrolyzing enzyme in the sample by any means known in the art, such as by a colorimetric, enzymatic or viscometric assay, but also quantifying its activity or concentration. Activity or concentration can be measured by comparing a viscosity curve obtained from a sample to control and standard curves. The methods can be performed on any polysaccharide and its coordinate polysaccharide-hydrolyzing enzyme.

As in this embodiment, "distinguish" or "distinguishing" means differentiating one plant from another (or more) by at least one chemical or physical property difference. For example, a first plant can be distinguished from another by comparing a viscosity curve from the first plant to a viscosity curve obtained from another plant by using the methods described herein. While not intending to be bound to any particular theory, plants from one plant variety will display a viscosity curve characteristic of that plant variety under a defined set of conditions, which can be used to distinguish that plant variety from others.

In another embodiment, the present invention relates to methods of identifying a plant by comparing viscosity curves based on the activity of a polysaccharide-hydrolyzing enzyme present in the plant. The methods involve measuring viscosity changes in a solution obtained from the plant having a polysaccharide-hydrolyzing enzyme and an amount of polysaccharide. The solution can be at a temperature above a gelatinization temperature for the polysaccharide, and the viscosity changes can be measured for about ten seconds to about two minutes, such that a change in viscosity is indicative of the activity of the polysaccharide-hydrolyzing enzyme. The viscosity changes can be used to construct a viscosity curve for the plant, which then can be compared to known viscosity curves obtained under similar assay conditions from known plant varieties. Substantial similarities between the slopes of the curves can be used to identify the plant.

As used in this embodiment, "identify" or "identifying" means assigning a name to the plant such as genus and species. For example, a plant can be identified by comparing a viscosity curve from the plant to viscosity curves obtained from known plants using the methods described herein. If the plant has a viscosity curve that is substantially similar to one of the known plants, it can be said that the two plants are likely of the same variety.

In a related embodiment, the present invention relates to methods of identifying the source organism of a heterologous polysaccharide-hydrolyzing enzyme in a plant based on the activity of the heterologous polysaccharide-hydrolyzing enzyme. The methods involve measuring viscosity changes in a solution obtained from the plant having the heterologous polysaccharide-hydrolyzing enzyme and an amount of polysaccharide. The solution can be at a temperature above a gelatinization temperature for the polysaccharide, and the viscosity changes can be measured for about ten seconds to about two minutes, such that a change in viscosity is indicative of the activity of the polysaccharide-hydrolyzing enzyme. The viscosity changes can be used to construct a viscosity curve for the plant, which then can be compared to known viscosity curves obtained under similar assay conditions from polysaccharide-hydrolyzing enzymes of known source organisms. Substantial similarities between the slopes of the curves can be used to identify the source organism from which the heterologous polysaccharide-hydrolyzing enzyme originated.

As used in this embodiment, "identify" or "identifying" means assigning a name to the source organism from which the heterologous polysaccharide-hydrolyzing enzyme originated, such as if the enzyme is from a known plant variety or if the enzyme is from a thermophilic bacteria. For example, a polysaccharide-hydrolyzing enzyme in a plant can be identified by comparing a viscosity curve from the polysaccharide-hydrolyzing enzyme in the plant to viscosity curves obtained from polysaccharide-hydrolyzing enzymes in known source organisms using the methods described herein. If the plant has a viscosity curve that is substantially similar to one of the known source organisms, it can be said that the polysaccharide-hydrolyzing enzyme of the plant is the same as that of the source organism. While not intending to be bound to any particular theory, polysaccharide-hydrolyzing enzymes display a characteristic viscosity curve under a defined set of conditions, which can be used to identify the organism from which it originated.

As used herein, "polysaccharide" or "polysaccharides" means relatively complex carbohydrates that are polymers of monosaccharides (at least ten or more) joined together by glycosidic bonds. They have a general formula of $C_x(H_2O)_y$, where x is usually a large number between about 200 and about 2500. Polysaccharides can be homopolysaccharides (i.e., comprised of one type of monosaccharide) or heteropolysaccharides (i.e., comprised of more than one type of monosaccharide). Examples of polysaccharides include, but are not limited to, arabinans, celluloses, chitins, chitosans, dextrans, dextrins, galactans, glycogen, gums, hyaluronic acid, lignin, pectin, starch and mixtures thereof. The examples below describe proof-of-concept with corn starch.

As used herein, "polysaccharide-hydrolyzing enzyme" or "polysaccharide-hydrolyzing enzymes" means enzymes that cleave polysaccharides by adding water, thereby degrading polysaccharides into their monosaccharide components. Examples of polysaccharide-hydrolyzing enzymes include, but are not limited to, amylases, cellulases, chitinases, chitosanases, glucoamylases, glucosidases, glycogen phosphorylases, glycoside hydrolases and hyaluronidase. The examples below describe proof-of-concept with amylase.

The polysaccharide-hydrolyzing enzyme can be prepared from a plant material/part (e.g., grain or seed) by any method known in the art such as grinding or milling, which exposes (i.e., liberates) the enzyme and any endogenous polysaccharide. Johnston & Singh (2004) *Cereal Chem.* 81:626-632; Singh et al. (2005) *Cereal Chem.* 82:187-190; Singh et al. (2006) *Cereal Chem.* 83:317-320; and Singh et al. (2006) *Cereal Chem.* 83:321-323. Typically, one can use between about 10 g to about 250 g of grain, depending upon the desired level of detection. In addition, one can obtain a moisture content of the plant material by a moisture analyzer such as a HB43 Halogen Moisture Analyzer (Mettler Toledo; Columbus, Ohio). In contrast to conventional methods of measuring polysaccharide hydrolysis, the methods described herein do not require that the polysaccharide-hydrolyzing enzyme be extracted or purified from the plant material/part, do not require exogenous polysaccharide substrate, and do not require complete hydrolysis of the polysaccharide.

Of particular interest herein are α-amylases, especially high-temperature (i.e., thermotolerant) α-amylases, which hydrolyze starch to a mixture of maltose, maltotriose and dextrin. α-amylases play a key role in the metabolism of plants by hydrolyzing starch in the germinating seed and in other plant tissues, which is accomplished primarily through the 1,4-α endoglycolytic cleavage of amylose and amylopectin, the principal components of starch granules in plant cells. Multiple α-amylases have been detected in corn, rice, wheat, barley and other cereals. See, e.g., Huang et al. (1992) *Proc. Natl. Acad. Sci. USA* 89:7526-7530.

Thermotolerant α-amylases have been identified that display performance characteristics ideal for a corn wet milling process. See, Richardson et al. (2002) *J. Biol. Chem.* 277 (29):26501-26507. Additionally, genetically modified plants have been developed in which a thermotolerant α-amylase enzyme is introduced into the plants. These plants perform well in fermentation without the addition of exogenous α-amylase, require much less time for liquefaction, and result in more complete solubilization of starch. See, e.g., U.S. Pat. No. 7,102,057 and US Patent Application Publication No. 2006/0230473.

Suitable α-amylases include, but are not limited to, naturally occurring α-amylases as well as recombinant or mutant amylases that are useful in liquefaction of starch. For example, the α-amylase can be the α-amylase described in Richardson et al. ("797GL3"). See, Richardson et al. (2002), supra. Alternatively, the α-amylase can be the α-amylase described in Atichokudomchai et al. ("D45"). See, Atichokudomchai et al. (2006) *Carbohyd. Polym.* 64:582-588; see also, US Patent Application Publication Nos. 2003/0125534 and 2004/0018607, which describe numerous other α-amylases that may be analyzed using the methods described herein.

Alternatively still, α-amylases can be derived from the microorganism order Thermococcales. Amylases are produced by a wide variety of other microorganisms including, but not limited to, *Bacillus* spp. and *Aspergillus* spp., with most commercial amylases being produced from bacterial sources such as *Bacillus licheniformis, Bacillus amyloliquefaciens, Bacillus subtilis* and *Bacillus stearothermophilus.*

Methods for producing variant amylases also are known in the art. See, e.g., Berk & Lebbink (2003) *Methods Mol Biol.* 230:1064-3745; Matsui et al. (1992) *FEBS Lett.* 310: 216-215; US Patent Application Publication No. 2009/0275078 and U.S. Pat. Nos. 5,958,739 and 7,601,527. Such methods can be utilized to alter the hydrolysis properties of known amylase enzymes to suit the needs of the present invention.

Additionally, polynucleotides encoding the characterized α-amylases described herein or otherwise known in the art can be used to isolate homologous sequences from cultured organisms or environmental samples. For example, gene libraries generated from one or more α-amylase-expressing microorganisms can be screened for amylase enzymes exhibiting a particular hydrolysis pattern. Methods for making and using organisms expressing α-amylase enzymes (e.g., to produce fermentable substrates for the production of ethanol) also are provided in US Patent Application Publication No. 2003/0135885.

The sample having the polysaccharide-hydrolyzing enzyme and/or polysaccharide can be from any source. Of particular interest herein are samples from plant material/part of any plant variety including genetically modified plants. As used herein, "genetically modified plant" means a plant that has incorporated or integrated at least one nucleic acid sequence, segment or construct into at least one cell of the plant. Examples of genetically modified plants include, but are not limited to, hybrid plants, recombinant plants and transgenic plants. The nucleic acid sequence or DNA segment or construct can be homologous or heterologous to the plant. A "homologous" nucleic acid sequence, segment or construct is a nucleic acid sequence naturally associated with a plant cell into which it is introduced. The homologous nucleic acid sequence can be under the control of its natural expression control element or a heterologous expression control element (i.e., promoter and enhancers). In contrast, a "heterologous" nucleic acid sequence is a nucleic acid sequence not naturally associated with the plant cell into which it is introduced (i.e., from a source foreign to the particular host plant or plant part), including non-naturally occurring multiple copies of a naturally occurring nucleic acid sequence. As such, a heterologous nucleic acid sequence is not endogenous to the plant or plant cell. Heterologous also means a polypeptide that is foreign to the plant, or homologous to the plant but in a position within the plant's genome in which it is not ordinarily found.

As used herein, "hybrid" means a plant that has been genetically modified by crossing a first plant variety with a second plant variety to introduce at least one nucleic acid molecule from the second plant variety's genome into the first plant variety's genome. The at least one nucleic acid molecule can be a naturally occurring nucleic acid molecule. As used herein, "naturally occurring" means a nucleic acid molecule having a sequence that is substantially identical to its natural (i.e., wild-type) sequence. Alternatively, the at least one nucleic acid molecule can be a non-naturally occurring nucleic acid molecule. As used herein, "non-naturally occurring" means a nucleic acid molecule having a sequence that has been modified from its natural sequence such as by an insertion, deletion, duplication, combination of two otherwise separate nucleic acid sequences, etc. Regardless of whether the nucleic acid molecule is naturally or non-naturally occurring, it is passed from one plant variety to another by crossing. It is intended that any hybrid plant having a polysaccharide-hydrolyzing enzyme is suitable for use herein.

As used herein, "recombinant" means a plant that has been genetically modified by introducing into the plant's genome at least one nucleic acid molecule. The nucleic acid molecule can be a naturally or non-naturally occurring nucleic acid molecule from a plant as described above and can be homologous or heterologous to the plant. It is intended that any recombinant plant having a polysaccharide-hydrolyzing enzyme is suitable for use herein.

As used herein, "introducing" means introducing nucleic acid molecules into a plant by non-biological means. Examples of such non-biological means of introducing nucleic acids into plants includes, but is not limited to, electroporation, particle bombardment; bacterial transformation such as *Agrobacterium*-mediated transformation, and viral transformation with a suitable plant virus. Methods for transforming plants by any of these methods are known in the art. See, e.g., D'Halluin et al. (1992) *Plant Cell,* 4:1495-1505; Gelvin (2005) *Nat. Biotechnol.* 23:684-685; Gleba et al. (2004) *Curr. Opin. Plant. Biol.* 7:182-188; Huang & Wei (2005) *Plant Cell Tiss. Org.* 83:187-200; Ishida et al. *Nat. Biotechnol.* (1996) 14:745-50.; Klein et al. (1989) *Plant Physiol.* 91:440-444; Klein et al. (1992) *Bio/Technology* 10:286-291; Marillonnet et al. (2005) *Nat. Biotechnol.* 23:718-723; Porta & Lomonossoff (2002) *Biotechnol. Genet. Eng. Rev.* 19:245-291; and Van Wert & Saunders (1992) *Plant Physiol.* 99:365-367.

As used herein, "transgenic" means a plant that has been genetically modified by introducing into the plant's genome at least one nucleic acid molecule from a species other than a plant, such as from a bacteria or mammal. The nucleic acid molecule can be naturally or non-naturally occurring as described above and can be homologous or heterologous to the plant. When the nucleic acid molecule is homologous, it can be introduced at a site in the plant genome that is different from the naturally occurring site.

Any type of plant can be used as the source for the polysaccharide-hydrolyzing enzyme and/or polysaccharide. Examples of plants include, but are not limited to, maize (corn), wheat, rice, barley, soybean, cotton, sorghum, beans in general, rape/canola, alfalfa, flax, sunflower, safflower, millet, rye, sugarcane, sugar beet, cocoa, tea, tropical sugar beet, *Brassica* spp., cotton, coffee, sweet potato, flax, peanut, clover; vegetables such as lettuce, tomato, cucurbits, cassava, potato, carrot, radish, pea, lentils, cabbage, cauliflower, broccoli, Brussel sprouts, peppers, and pineapple; tree fruits such as citrus, apples, pears, peaches, apricots, walnuts, avocado, banana, and coconut; and flowers such as orchids, carnations and roses. Other plants useful in the practice of the invention include perennial grasses, such as switchgrass, prairie grasses, Indiangrass, Big bluestem grass, miscanthus and the like. It is recognized that mixtures of plants can be used.

The plant therefore can be a wild-type plant or can be genetically modified to have optimized polysaccharide content, optimized polysaccharide-hydrolyzing enzyme activity or both. See, e.g., Farago (2007) *Nova Biotechnologica* VII-I: 63-68; and US Patent Application Publication No. 2008/0201807. For example, corn event 3272 (Syngenta Biotechnology, Inc.; Research Triangle Park, N.C.) is modified to express a thermotolerant α-amylase (US Patent Application Publication No. 2006/0230473). Amylase, which is not normally present in corn, breaks starch down. Including amylase expression in corn can reduce the costs of ethanol production up to ten percent, as the addition of an exogenous amylase for ethanol production is not required or is reduced. A quick assay for corn amylase can further reduce the costs of ethanol production by eliminating the need to extract the enzyme from the modified corn prior to analysis to determine whether exogenous amylase is required for optimized ethanol production. A quick assay also allows the ethanol plant to quickly determine at which admix levels the grain must be introduced into the plant. For example, transgenic grain expressing a thermotolerant α-amylase (see, US Patent Application Publication No. 2006/0230473) would need to be quickly monitored to ensure that the enzyme is in fact present as well as to determine if adequate amounts of enzyme will be introduced into the mill.

As used herein, "plant material," "plant part" or "plant tissue" means plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like.

Briefly, a known concentration of a polysaccharide such as starch can be prepared as a solution so that it is hydrated and in a solubilized state. When heated to a pre-determined temperature (i.e., gelatinization temperature), the polysaccharide will generate a viscosity value that changes upon the addition of a polysaccharide-hydrolyzing enzyme such as amylase. A change in viscosity indicates that the given polysaccharide-hydrolyzing enzyme is present. Therefore, a pre-heated (i.e., above a gelatinization temperature of the polysaccharide) polysaccharide solution with a given viscosity can be used as a substrate to detect the polysaccharide-hydrolyzing enzyme in the sample.

As used herein, "gelatinization temperature" means that temperature at which a polysaccharide, such as starch granules, begins to lose its internal order and crystallinity, and becomes hydrated. Once gelatinized, the hydrated granules may increase the viscosity of the solution and/or associate to form gels. Gelatinization temperatures for various polysaccharides are known in the art. See, e.g., Heldman & Lund, *Handbook of food engineering* ($2^{nd}$ ed. CRC Press 2006).

Any method known in the art can be used to measure the chemical and/or physical properties of the reaction mixture or the reaction products. One can measure enzymatically released soluble sugar fragments in the reaction mixture. Enzymatic activity reflects the presence/hydrolytic activity of the polysaccharide-hydrolyzing enzyme. For example, one can measure the turbidity of the reaction mixture, which decreases upon hydrolysis. See, e.g., Schwimmer (1951) *J. Biol. Chem.* 188:477-484. Alternatively, one can measure an iodine/reaction product complex, or can use near-infrared (NIR) spectroscopy, a polarimeter or refractometer to measure soluble sugar fragments. See, Chinoy (1939) *Microchimica Acta* 26:132-142; Chung & Arnold (2000) *Appl. Spectrosc.* 54:277-283; Jansen et al. (2001) *Potato Research* 44:137-146; and Sugiura & Ooshiro (1999) *Shizuoka Prefect. Citrus Exp. Stn.* 28:11-17.

In addition, one can measure enzymatically released oligosaccharides such as malto-oligosaccharides in the reaction mixture. For example, one can measure oligosaccharides with Benedict's test. See, e.g., Benedict (1908) *J. Biol. Chem.* 5:485-487. Alternatively, one can measure oligosaccharides with a sensor specific for the oligosaccharide, such as a malto-oligosaccharide sensor. See, e.g., U.S. Pat. No. 5,081,037. Such sensors use optical or fluorescent detection. Alternatively still, one can measure oligosaccharides with NIR, high-performance liquid chromatography (HPLC) or size-exclusion chromatography. See, Hollung et al. (2005) *J. Agric. Food Chem.* 53:9112-9121; Ivanova et al. (1991) *Appl. Biochem. Biotechnol.* 30:193-202; and White et al. (2003) *J. Chromatogr. A.* 997:79-85.

Alternatively, one can measure the pressure required to pass the reaction product mixture through an aperture or filter, measure the speed of a falling sphere through the reaction mixture; measure the capillary action of the reaction mixture or measure the speed of an air bubble released from the bottom of the reaction vessel. See, Chang et al. (1999) *J. Sci. Food Agric.* 79:19-24; Maxworthy et al. (1996) *J. Fluid Mech.* 321:421-441; and U.S. Pat. Nos. 3,617,322 and 5,023,176.

Furthermore, and as shown below in the examples, one can measure the changes in viscosity of the reaction mixture. See, e.g., Sanromán et al. (1996) *Appl. Biochem. Biotechnol.* 59: 329-336; and Collado et al. (1990) *J. Agric. Food Chem.* 47:832-835. As used herein, "viscosity" means a measure of resistance of a fluid sample that is being deformed by either shear stress or extensional stress. In the methods described herein, the viscosity of the sample is proportional to its polysaccharide concentration such that increased polysaccharide concentration results in increased viscosity. A change in the integrity of the polysaccharide mediated by the polysaccharide-hydrolyzing enzyme therefore can be reflected by a decrease in the viscosity of the sample.

Methods

Methods are provided for distinguishing plants by obtaining viscosity curves based on the activity of a polysaccharide-hydrolyzing enzyme. The viscosity curves are obtained by measuring polysaccharide-hydrolyzing enzyme activity in a sample at a pre-determined temperature over a short, yet pre-determined, time. An assay for rapidly measuring polysaccharide-hydrolyzing enzyme activity is described in U.S. Provisional Patent Application No. 61/161,182 (filed Mar. 18, 2009) and can be used with the methods described herein.

Polysaccharides and polysaccharide-hydrolyzing enzymes are described above. The polysaccharide can be prepared as a solution and corresponds as a substrate for the polysaccharide-hydrolyzing enzyme of interest. For example, one can use starch for detecting α-amylase or can use cellulose for detecting cellulase. The polysaccharide, however, can be of a known or unknown amount or concentration. The polysaccharide solution can be above a gelatinization temperature for the polysaccharide. For example, the temperature of the polysaccharide solution can be above a gelatinization temperature, which can be from about 60° C. to about 100° C., about 70° C. to about 95° C., about 80° C. to about 90° C. or about 85° C., about 90° C., about 95° C. or about 99° C. The temperature can be modified to achieve different response curves, but typically should not exceed about 105° C. As used herein, "about" means within a statistically meaningful range of a value such as a stated concentration range, time frame, molecular weight, volume, temperature or pH. Such a range can be within an order of magnitude, typically within 20%, more typically still within 10%, and even more typically within 5% of a given value or range. The allowable variation encompassed by "about" will depend upon the particular system under study, and can be readily appreciated by one of skill in the art.

As also described above, polysaccharide-hydrolyzing enzyme, and in some cases even the polysaccharide, can be prepared from a plant material or part (e.g., grain or seed) by any method known in the art, such as grinding or milling.

The polysaccharide-hydrolyzing enzyme can be added to the solution having a known polysaccharide concentration, or through the processing of a plant part, the polysaccharide-hydrolyzing enzyme can contact its corresponding polysaccharide substrate endogenous to the plant part in the solution. Examples of aqueous materials suitable for making the polysaccharide/polysaccharide-hydrolyzing enzyme solution include, but are not limited to, water and saline. Regardless of the aqueous material used, it should not contribute significantly to overall viscosity of the solution, as high viscosity can interfere with the reaction. As such, the aqueous material preferably has a viscosity near that of water.

Briefly, a sample from a first plant can be prepared as a solution having a polysaccharide and a polysaccharide-hydrolyzing enzyme, which when heated to a pre-determined temperature, will generate a viscosity value that will change depending upon the activity or concentration of the polysaccharide-hydrolyzing enzyme. If the endogenous polysaccharide concentration is known to be low, one can add exogenous polysaccharide. Regardless, the rate of viscosity decrease will be directly related to the polysaccharide-hydrolyzing enzyme concentration and activity at a given polysaccharide concentration. A viscosity curve (i.e., time plotted on the abscissa and viscosity plotted on the ordinate; or activity plotted on the abscissa and viscosity plotted on the ordinate) generated over a short time period (e.g., ten seconds to two minutes) can be compared to a viscosity curve from a second plant that was obtained in the same manner. If the plants are of different varieties, the viscosity curves will have different slopes, thereby distinguishing the first plant from the second plant. In contrast, if the viscosity curves have substantially similar slopes, the first and second plant are likely of the same variety.

To begin, an aliquot of a solution having the polysaccharide and polysaccharide-hydrolyzing enzyme can be dispensed into a reaction vessel that can monitor the viscosity, agitation speed and temperature of the solution such as a Rapid Visco-Analyzer-4 (RVA-4; Newport Scientific; Jessup, Md.), computer-equipped with Thermocline Software (Newport Scientific). The RVA-4 continuously measures apparent viscosity under variable conditions of shear and temperature. Alternatively, the solution can be dispensed into a reaction vessel that can monitor the turbidity, agitation speed and temperature of the solution such as an Optec® DT9011 Laboratory Turbidity Meter (Optec; Germantown, Wis.).

The reaction proceeds for only a short period of time to ensure only partial hydrolysis of the polysaccharide. As such, the reaction can be performed for a time of less than about five minutes, less than about four minutes, less than about three minutes, less than about two minutes, or less than about one minute. Alternatively, the reaction can be from about ten seconds to about three minutes, from about fifteen seconds to about two minutes, or from about thirty seconds to about one minute. Preferably, the reaction can be from about ten seconds to about three minutes or from about ten seconds to about two minutes. During this time, continuous viscosity measurements can be monitored over a course of time as described above. A decrease in viscosity is directly related to the presence and activity of the polysaccharide-hydrolyzing enzyme of interest. In the examples below, α-amylase was detected by changes in viscosity in a starch solution.

Methods of measuring the viscosity and/or enzymatically released soluble sugar fragments are described above. Likewise, methods of quantifying the viscosity and/or enzymatically released soluble sugar fragments are described above. In these methods, however, standard and control curves can be prepared beforehand with known concentrations of polysaccharide and known concentrations of polysaccharide-hydrolyzing enzyme.

In some instances, a set of standard curves with various concentrations of polysaccharide and/or polysaccharide-hydrolyzing enzyme can be prepared. Standard curves can be generated under identical reaction conditions from extracted, commercially available polysaccharide-hydrolyzing enzymes (e.g., liquid amylase, available from Sigma; St. Louis, Mo.).

In some instances, calibrations curves may be required. Calibration curves can be generated from samples having a known polysaccharide-hydrolyzing enzyme concentration and correlating concentration with viscosity. For example, an amylase standard (e.g., liquid amylase, available from Sigma; St. Louis, Mo.) can be made or purchased having a known concentration and dosed into a corn slurry containing starch. Viscosity measurements therefore can be monitored over the course of time as described above. A calibration curve then can be charted by plotting a relative viscosity measurement to its corresponding enzyme concentration of the known amylase standard. This calibration curve then can be used to calculate amylase activity or concentration using only viscosity readings over a certain time point using endogenous starch as a substrate.

In some instances, the polysaccharide can be endogenous to the plant material from which the polysaccharide solution is made or can be exogenous and added to the polysaccharide solution at a known concentration. When the polysaccharide is exogenous to the solution, it can be at a concentration of about at least 140 mg/g total weight.

Methods also are provided for identifying a plant variety or for identifying a source organism from which a heterologous polysaccharide-hydrolyzing enzyme originates.

Briefly, a sample from a plant variety having a native (i.e., homologous) or heterologous polysaccharide-hydrolyzing enzyme can be prepared as a solution having a polysaccharide, which when heated to a pre-determined temperature, will generate a viscosity value that will change depending upon the activity or concentration of the polysaccharide-hydrolyzing enzyme. If the endogenous polysaccharide concentration is known to be low, exogenous polysaccharide can be added as described above. Regardless, the rate of viscosity decrease will be directly related to the enzyme activity or concentration at a given polysaccharide concentration. A viscosity curve generated over a short time period (i.e., ten seconds to two minutes) can be compared to viscosity curves obtained in the same manner from known plant varieties. If the plant is of the same variety as the known plant variety, the viscosity curves will be substantially similar in slope. Thus, the plant variety can be identified by its viscosity curve obtained by polysaccharide-hydrolyzing enzyme activity.

Likewise, a viscosity curve generated over a short time period (i.e., ten seconds to two minutes) can be compared to viscosity curves obtained in the same manner from known source organisms having a polysaccharide-hydrolyzing enzyme of interest. If the plant variety has a heterologous polysaccharide-hydrolyzing enzyme from a known source organism, the viscosity curves will be substantially similar in slope to the viscosity curve from the known source organism from which the heterologous polysaccharide-hydrolyzing enzyme originated. Thus, the source organism of the heterologous polysaccharide-hydrolyzing enzyme in the plant variety can be identified.

The viscosity curve of the known plant variety or source organism can be obtained simultaneously with the plant sample or can be previously obtained and stored, for example, in a database.

The reaction conditions are described above in which the reaction proceeds for a short period of time to ensure only partial hydrolysis of the polysaccharide. As such, viscosity measurements can be monitored and/or quantified over the course of time as described above. Standard curves can be generated under identical reaction conditions from extracted, commercially available polysaccharide-hydrolyzing enzymes (e.g., liquid amylase, available from Sigma; St. Louis, Mo.). A set of standard curves can be made with various concentrations of polysaccharide and/or polysaccharide-hydrolyzing enzyme. The standards can be prepared beforehand with known concentrations of polysaccharide and/or known concentrations of polysaccharide-hydrolyzing enzyme. Alternatively, enzymatically released soluble sugar fragments can be monitored and/or quantified as described above.

As above, these methods contemplate the use not only of unextracted polysaccharide-hydrolyzing enzyme from the plant material, but also of endogenous polysaccharide, although in some instances it can be appropriate to add exogenous polysaccharide.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

In some instances enzyme activity can be quickly correlated to glucose levels. This may be useful for example in the embodiments described herein where enzyme activity is measured along with viscosity to create a standard curve for a first plant which can then be compared to a database of standard curves wherein said first plant may be identified or distinguished from another second plant by comparing slopes of said standard curves. In this instance glucose levels may be measured and correalated to a "enzyme activity standard curve" that plots glucose levels with known amylase activities. An enzyme activity standard curve may be constructed for example by creating various admixes of corn flour containing a thermophilic alpha-amylase (e.g. 25%, 50%, 75%, and 100% admix) and measuring admixes for amylase activity using a colorimetric assay such as Amylazyme™ (Megazyme; Wicklow, Ireland). Water can then be added to the respective admixed flour to make a corn slurry at approximately 28% dry solids. Next, mix and heat said corn slurry for a pre-determined time (e.g. 60 seconds at 80° C. to 95° C.). Following 60 seconds, glucose levels could be measured quickly using a commercially available glucose meter (e.g. ReliOn® Ultima Glucose Meter (ReliOn)). Extrapolate the amylase activity for each admix level and glucose data onto a X/Y axis curve. This enzyme activity curve could then be used to quickly correlate glucose level with amylase activity.

All of the patents, patent applications, patent application publications and other publications recited herein are hereby incorporated by reference as if set forth in their entirety.

EXAMPLES

Example 1: Modified Fast Assay for Amylase

Methods.
Modified Fast Assay for Corn Amylase:
approximately 200 g of seed was ground (i.e., dry milled) separately for each hybrid to flour in a Perten® 3600 Disc Mill (setting 0; Perten Instruments AB; Huddinge, Sweden). Next, approximately 9 g of flour was weighed into a Strarchmaster® 2 Viscometer (Newport Scientific Pty. Ltd.; Warriewood, Australia) and mixed with water to create a 28% dry solids corn slurry. The corn slurry has an acceptable buffering capacity, so it was not necessary to add agents to control pH.

The temperature of the corn slurry reaction mixture in the viscometer was set to 80° C. with continued agitation and a gradual ramping up of the temperature to 95° C. The test profile was carried out as shown in Table 1.

TABLE 1

Test profile for viscosity measurements in corn amylase.

| Time (min:sec) | Temperature (° C.) | Agitation Speed (rpm) |
|---|---|---|
| 00:00 | 80 | 960 |
| 00:04 | Ramp to 95 | 160 |
| 01:14 | 95 | 160 |
| 01:14 | END | — |

Viscosity, agitation speed and temperature of the reaction mixture were measured at one second intervals as the hydrolysis reaction proceeded for a total of 74 seconds. Assays on the seven admixtures were run in triplicate and the generated viscosity curves are shown in FIG. 1.
Results.
As shown in FIG. 1, viscosity decreased in proportion to the amount of corn amylase in a sample. Viscosity of the various samples was estimated by using the following equation: $CA=\{121.30-(14713.69-2.296(7972.96-\text{viscosity}))^{1/2}\}/1.148$.

Example 2: Modified Fast Assay for Corn Amylase Using a Standard Coffee Maker

Methods.
Corn Amylase Assay in Standard Coffee Maker:
15 g of corn flour containing a thermo-tolerant α-amylase is added to a coffee filter fitting a standard 4 cup coffee maker such as a Mr. Coffee® 4-Cup Dispenser (Sunbeam Products, Inc.) (or any non-programmable standard coffee maker). 60 g of tap water is then added to the pre-heated coffee machine. The vaporized water is collected in the filter container with the pre-weighed corn flour and held for 1-3 minutes before dispensing. Pressure is applied to the filter to ensure full liquid collection.

Amylase Quantification:

The collected sample from the coffee machine is mixed and a glucose meter is used to determine the glucose concentration, which can be used to determine the dose of amylase in the flour. A glucose meter such as the ReliOn® Ultima Glucose Meter (ReliOn) may be used for measuring glucose levels. The glucose meter is used according to the manufacturer's directions: a strip is fitted into the meter and dipped into the collected sample. Processing time takes about 5 seconds. A standard curve of glucose vs. amylase dose can be used to quantify an unknown sample dose.

Figure 2:
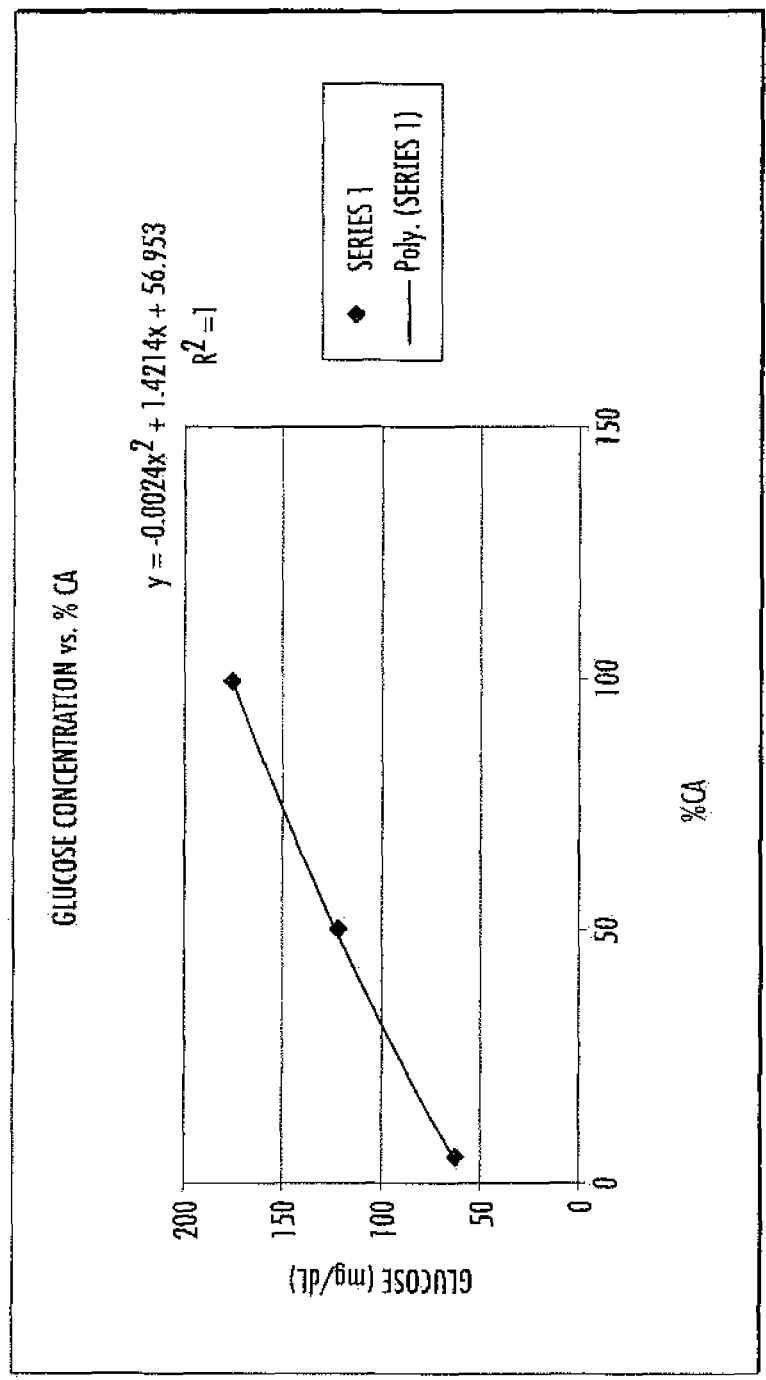
FIG. 2 shows glucose values related to known doses of thermotolerant α-amylase.

If glucose values are below the meter's detection limit, a saccharification step is added. A known amount of excess commercial glucoamylase is added to a specific volume of the collected sample. The sample is incubated at 40° C. for 1 minute, followed by either direct sample reading or a dilution and then sample reading. A separate standard curve would need to be generated, as shown in FIG. 2.

Example 3: Generation of Maize Hybrid Standard Curves

Standard curves correlating viscosity with alpha-amylase activity were generated for three corn hybrids grown in various environmental conditions expressing a thermophilic α-amylase, 797GL3 (See FIGS. 3-10). It is intended to use the resulting standard curves to quickly distinguish one hybrid from another by measuring viscosity over a predetermined period of time (approximately 74 seconds) in the presence of an alpha-amylase. Thus for example, one could identify an unknown maize hybrid expressing a thermophilic α-amylase by 1) grinding seed of unknown hybrid (10-100 grams is sufficient) to flour; 2) Weigh approximately 9-20 grams of flour into a viscometer such as a Starchmaster® 2 Viscometer (Newport Scientific Pty. Ltd.; Warriewood, Australia); 3) mix with water to create a 28% dry solids corn slurry; 4) continue agitation via a gradual ramping up of the temperature to 95° C. (for example as shown in Table 1) measuring final viscosity at 74 seconds; 5) measure amylase activity either by colorimetric methods (i.e. Amylazyme™ (Megazyme; Wicklow, Ireland)), or the methods as described in either Examples 1 or 2; 6) extrapolate final viscosity data point and amylase activity data onto database of known standard curves 7) identify unknown hybrid by matching data points with standard curve associated with a known hybrid.

Multiple corn hybrids (i.e., X48005, X50115 and X51005) expressing a thermophilic α-amylase, 797GL3, were generated via plant sexual crossings. The hybrids were grown, and seed expressing 797GL3 were collected from each hybrid, respectively.

The hybrids were cultivated in the following locations: Arlington, Wis. for X48005 and X50115; Bluffton, Ind. for X50115 and X51005; Keystone, Iowa for X48005, X50115 and X51005; McLean, Ill. for X48005, X50115 and X51005; Milford, Iowa for X48005 and X50115; and Wyoming, Ill. for X50115 and X51005.

Seed (approximately 200 grams) from each hybrid was ground (i.e., dry milled) separately to flour in a Perten® 3600 Disc Mill (setting 0; Perten Instruments AB; Huddinge, Sweden). Next, flour from each hybrid was separately admixed into a negative isoline of the same hybrid type at approximately 25%, 50%, 75% and 100% admix ratio (for example, 10 g of flour expressing an alpha-amylase admixed with 90 grams of negative isoline flour would make up a 10% admix). Each admix was then assayed for amylase activity (U/g) using a commercially available amylase kit, Amylazyme™ (Megazyme; Wicklow, Ireland), according to the manufacturer's instructions. See also, McCleary & Sheehan (1989) *J. Cereal Sci.* 6:237-251. Following, 9 grams of admix was weighed out for each hybrid admix and placed into a Starchmaster® 2 Viscometer (Newport Scientific Pty. Ltd.; Warriewood, Australia). Water was then added to the sample mix to create a 28% dry solids corn slurry. Following the addition of water the sample undergoes continuous agitation via a gradual ramping up of the temperature to 95° C. as depicted in Table 1. Following 74 seconds of constant mixing, viscosity of the sample was measured for the relative admix. A standard curve can then be plotted by correalating amylase activity (U/g) for each admix level to viscosity at 74 seconds (See FIGS. 3-10). Table 2 provides the raw amylase activity and viscosity data for corn hybrids X48005, X50115 and X51005.

TABLE 2

Raw Amylase Activity and Viscosity Data for Three Corn Hybrids.

| Location | Hybrid | Activity (U/g) | Viscosity at 74 seconds | In CA activity | In Viscosity at 74 seconds |
|---|---|---|---|---|---|
| Arlington WI | X48005 | 12.9 | 958.5 | 2.56 | 6.87 |
| | | 25.8 | 613 | 3.25 | 6.42 |
| | | 38.6 | 480 | 3.65 | 6.17 |
| | | 51.5 | 461 | 3.94 | 6.13 |
| Keystone IA | X48005 | 13.2 | 1893.5 | 2.58 | 7.55 |
| | | 26.5 | 863 | 3.28 | 6.76 |
| | | 39.7 | 646.5 | 3.68 | 6.47 |
| | | 52.9 | 489.5 | 3.97 | 6.19 |
| McLean IL | X48005 | 11.4 | 1357.5 | 2.43 | 7.21 |
| | | 22.8 | 686 | 3.13 | 6.53 |
| | | 34.2 | 502.5 | 3.53 | 6.22 |
| | | 45.6 | 473.5 | 3.82 | 6.16 |
| Milford IA | X48005 | 10.7 | 1334 | 2.37 | 7.20 |
| | | 21.4 | 617 | 3.06 | 6.42 |
| | | 32.1 | 429.5 | 3.47 | 6.06 |
| | | 42.8 | 373 | 3.76 | 5.92 |
| Bluffton IN | X50115 | 10.4 | 805 | 2.34 | 6.69 |
| | | 20.9 | 460.5 | 3.04 | 6.13 |
| | | 31.3 | 413 | 3.44 | 6.02 |
| | | 41.7 | 368 | 3.73 | 5.91 |
| Keystone IA | X50115 | 9.3 | 1283 | 2.23 | 7.16 |
| | | 18.6 | 607.5 | 2.92 | 6.41 |
| | | 27.9 | 523.5 | 3.33 | 6.26 |
| | | 37.2 | 441.5 | 3.62 | 6.09 |
| McLean IL | X50115 | 9.9 | 1191.5 | 2.29 | 7.08 |
| | | 19.8 | 517 | 2.99 | 6.25 |
| | | 29.7 | 412.5 | 3.39 | 6.02 |
| | | 39.6 | 368.5 | 3.68 | 5.91 |
| Wyoming IL | X50115 | 10.6 | 806.5 | 2.36 | 6.69 |
| | | 21.2 | 504 | 3.05 | 6.22 |
| | | 31.8 | 427 | 3.46 | 6.06 |
| | | 42.4 | 304 | 3.75 | 5.72 |
| Arlington WI | X50115 | 10.2 | 960.5 | 2.33 | 6.87 |
| | | 20.5 | 576.5 | 3.02 | 6.36 |
| | | 30.7 | 501 | 3.43 | 6.22 |
| | | 41.0 | 413 | 3.71 | 6.02 |
| Milford IA | X50115 | 9.5 | 1283 | 2.25 | 7.16 |
| | | 18.9 | 545.5 | 2.94 | 6.30 |
| | | 28.4 | 422.5 | 3.35 | 6.05 |
| | | 37.9 | 349 | 3.63 | 5.86 |
| Bluffton IN | X51005 | 11.0 | 1115 | 2.40 | 7.02 |
| | | 21.9 | 629.5 | 3.09 | 6.44 |
| | | 32.9 | 376 | 3.49 | 5.93 |
| | | 43.9 | 331.5 | 3.78 | 5.80 |
| Keystone IA | X51005 | 12.0 | 1300.5 | 2.49 | 7.17 |
| | | 24.0 | 679 | 3.18 | 6.52 |
| | | 36.1 | 490 | 3.59 | 6.19 |
| | | 48.1 | 387.5 | 3.87 | 5.96 |
| McLean IL | X51005 | 10.9 | 1103 | 2.39 | 7.01 |
| | | 21.8 | 679.5 | 3.08 | 6.52 |
| | | 32.7 | 544 | 3.49 | 6.30 |
| | | 43.6 | 421.5 | 3.78 | 6.04 |

TABLE 2-continued

Raw Amylase Activity and Viscosity Data for Three Corn Hybrids.

| Location | Hybrid | Activity (U/g) | Viscosity at 74 seconds | In CA activity | In Viscosity at 74 seconds |
|---|---|---|---|---|---|
| Wyoming IL | X51005 | 13.5 | 724 | 2.60 | 6.58 |
| | | 26.9 | 513.5 | 3.29 | 6.24 |
| | | 40.4 | 420 | 3.70 | 6.04 |
| | | 53.9 | 302.5 | 3.99 | 5.71 |

Figure 3:
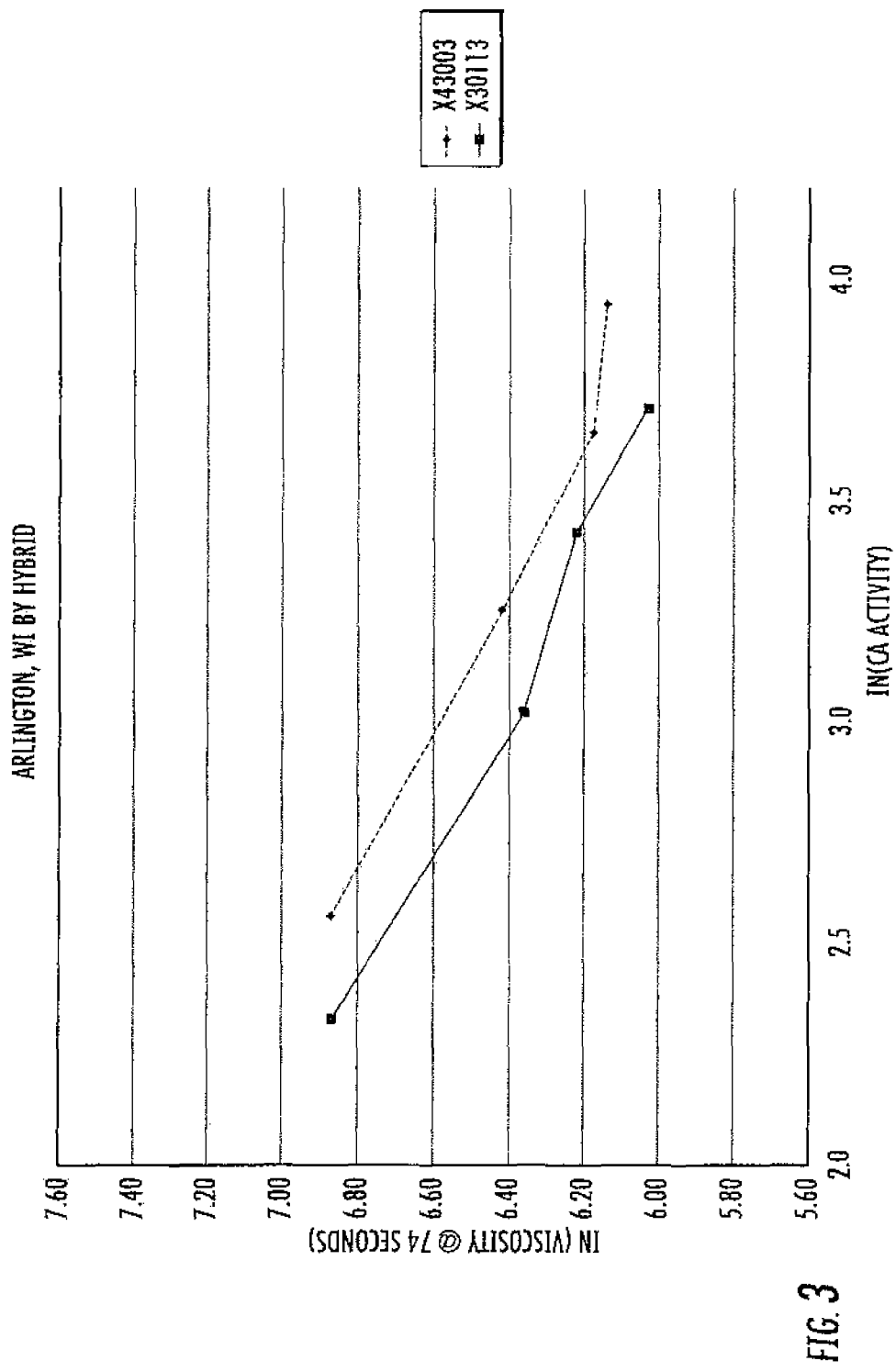
FIG. 3 shows viscosity changes between two corn hybrids (X48005 (diamonds) and X50015 (squares); n=4 for each hybrid) cultivated in Arlington, Wis. (abscissa is the natural logarithm (ln) of corn amylase (CA) activity; ordinate is the ln of viscosity at 74 seconds).
Figure 4:
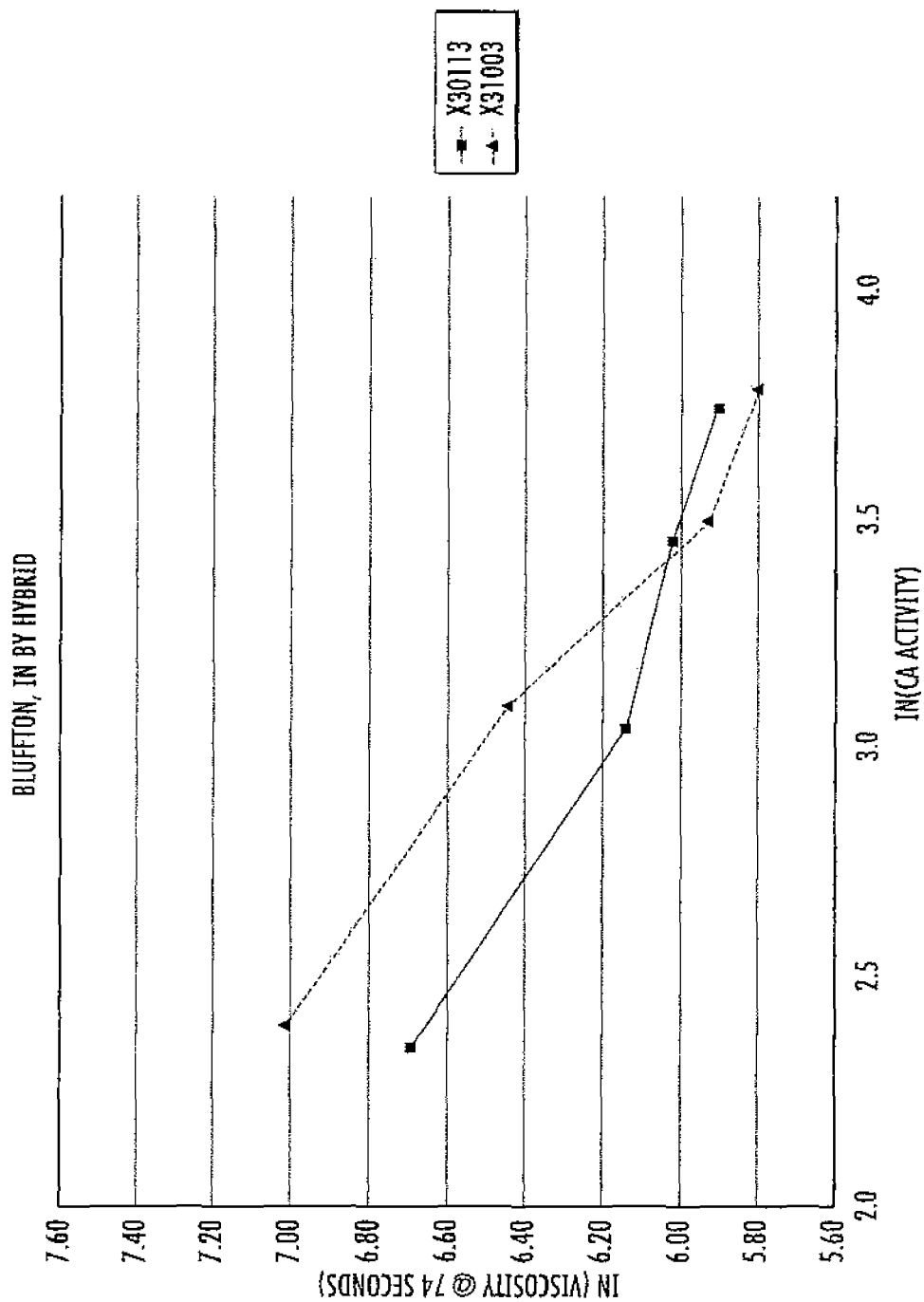
FIG. 4 shows viscosity changes between two corn hybrids (X50115 (squares) and X51005 (triangles); n=4 for each hybrid) cultivated in Bluffton, Ind. (abscissa is the ln of CA activity; ordinate is the ln of viscosity at 74 seconds).
Figure 5:
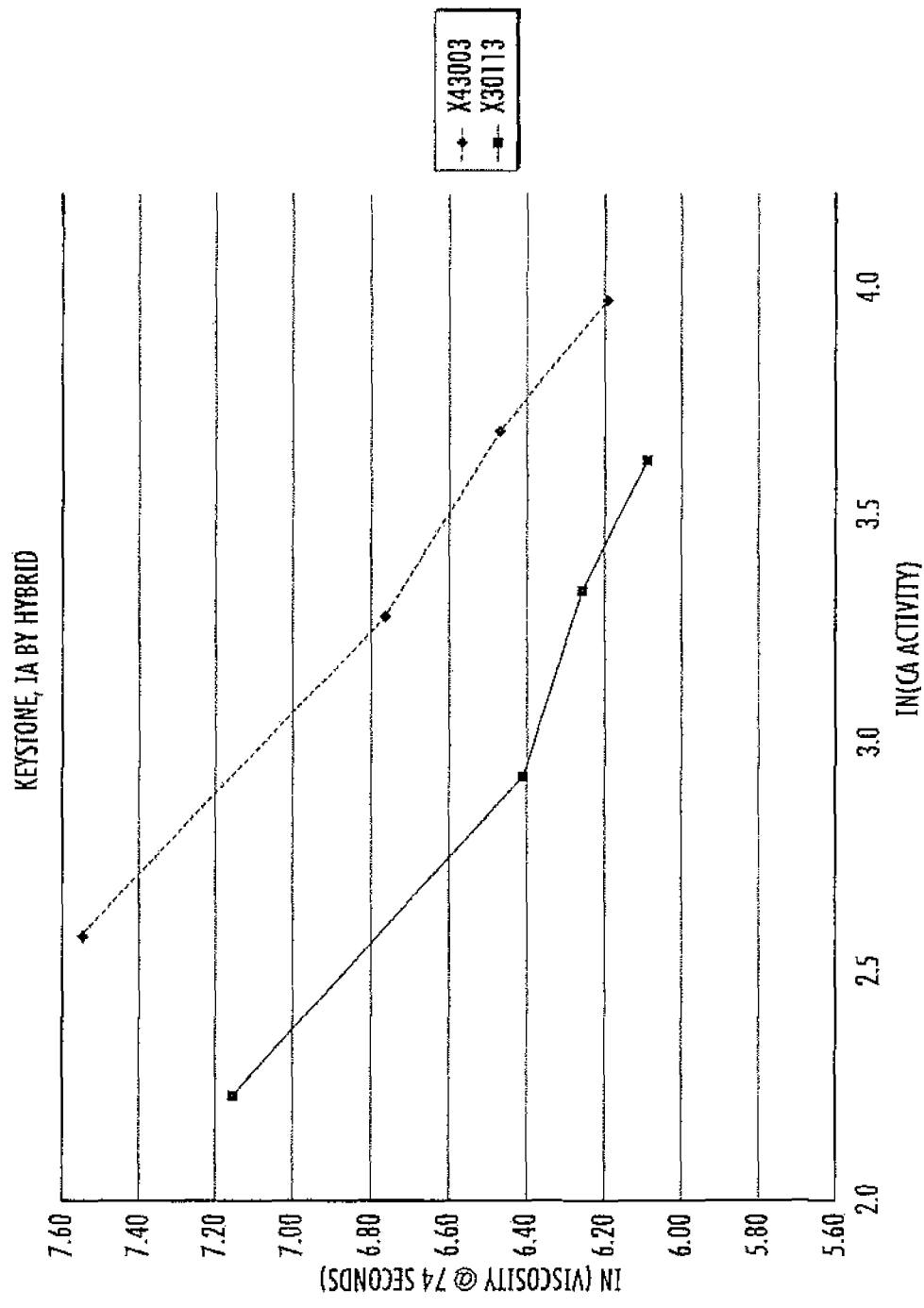
FIG. 5 shows viscosity changes between two corn hybrids (X48005 (diamonds) and X50115 (squares); n=4 for each hybrid) cultivated in Keystone, Iowa (abscissa is the ln of CA activity; ordinate is the ln of viscosity at 74 seconds).
Figure 6:
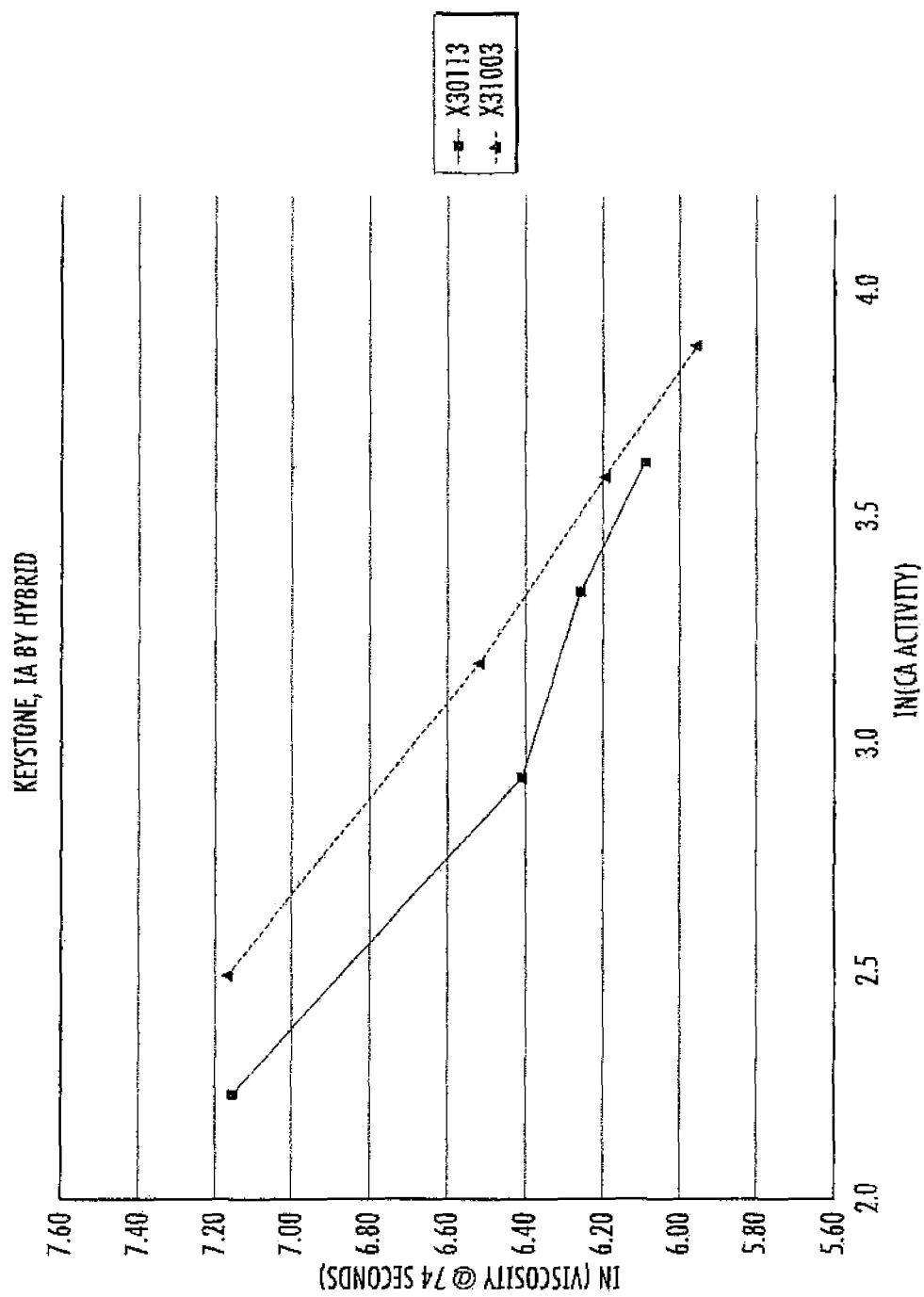
FIG. 6 shows viscosity changes between two corn hybrids (X50115 (squares) and X51005 (triangles); n=4 for each hybrid) cultivated in Keystone, Iowa (abscissa is the natural ln of CA activity; ordinate is the ln of viscosity at 74 seconds).
Figure 7:
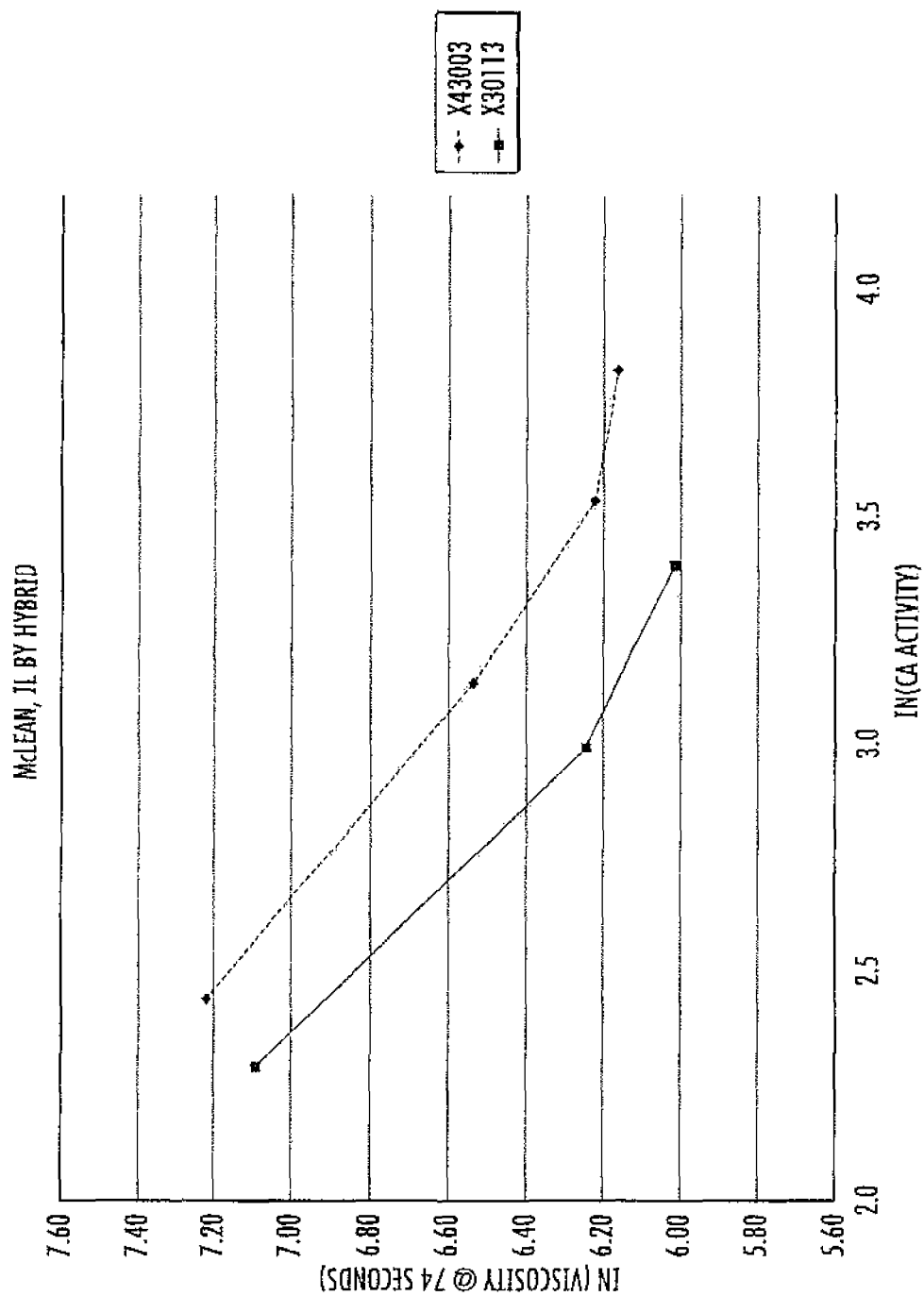
FIG. 7 shows viscosity changes between two corn hybrids (X48005 (diamonds) and X50115 (squares); n=4 for each hybrid) cultivated in McLean, Ill. (abscissa is the ln of CA activity; ordinate is the ln of viscosity at 74 seconds).
Figure 8:
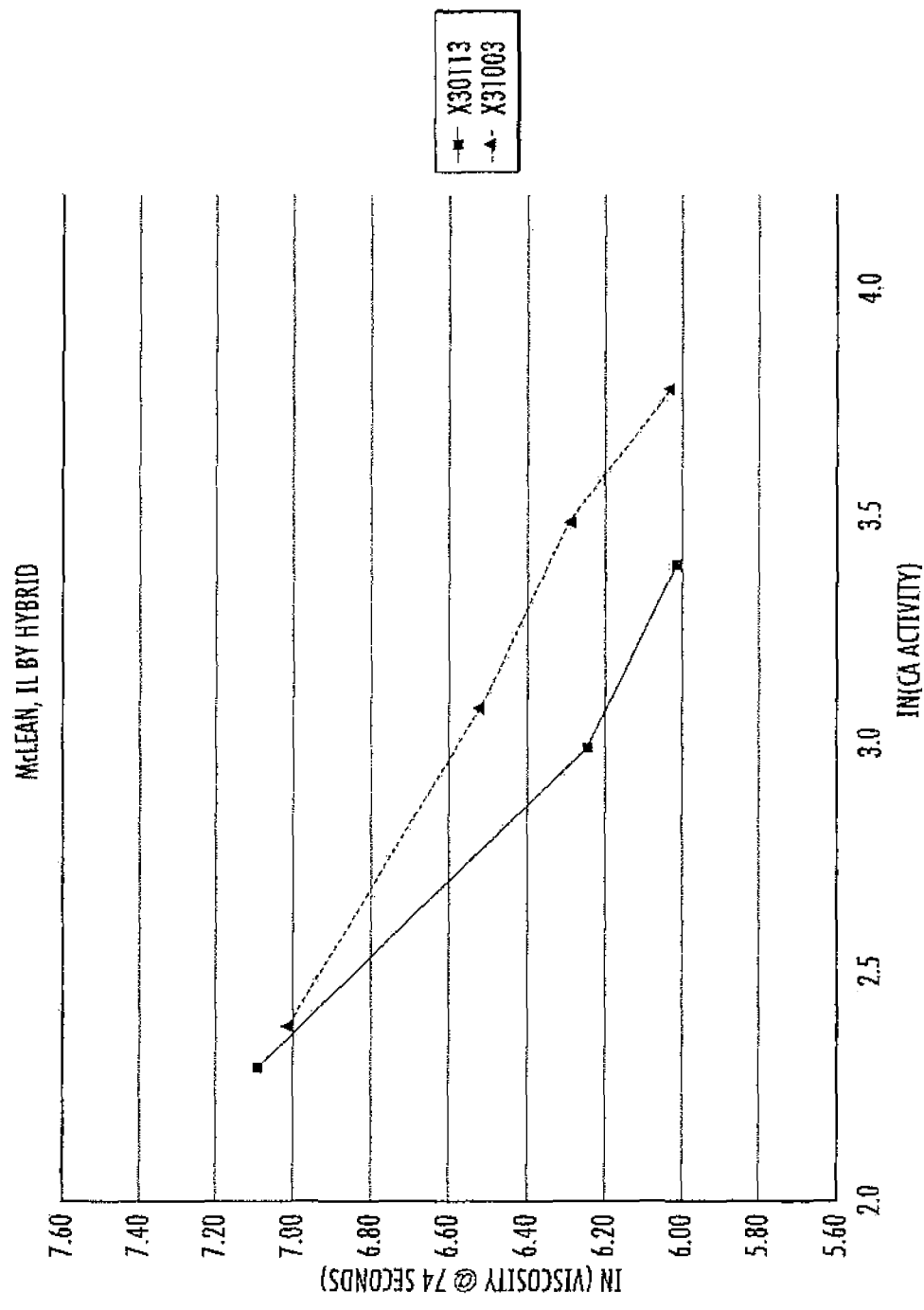
FIG. 8 shows viscosity changes between two corn hybrids (X50115 (squares) and X51005 (triangles); n=4 for each hybrid) cultivated in McLean, Ill. (abscissa is the natural ln of CA activity; ordinate is the ln of viscosity at 74 seconds).
Figure 9:
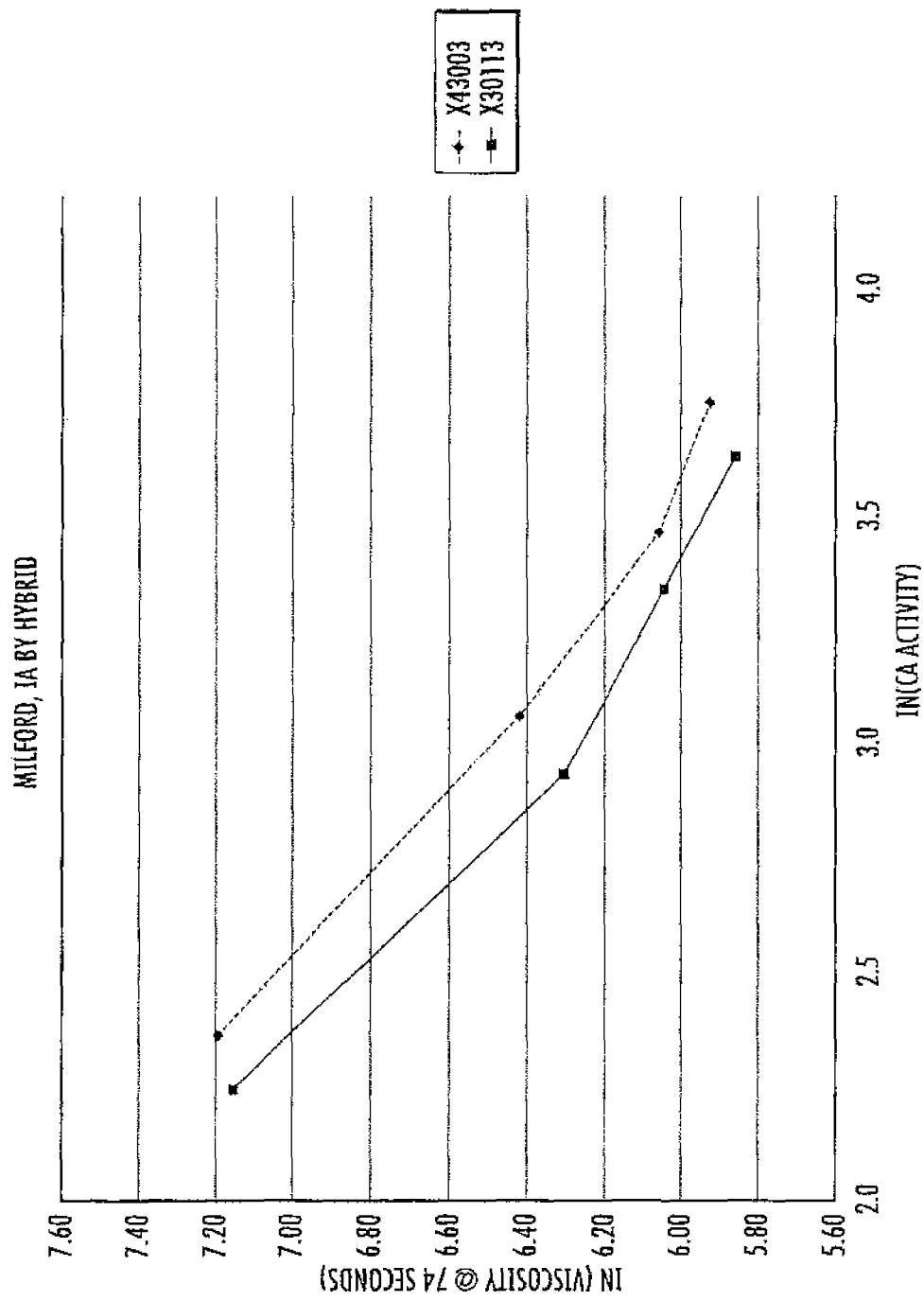
FIG. 9 shows viscosity changes between two corn hybrids (X48005 (diamonds) and X50115 (squares); n=4 for each hybrid) cultivated in Milford, Iowa (abscissa is the ln of CA activity; ordinate is the ln of viscosity at 74 seconds).
Figure 10:
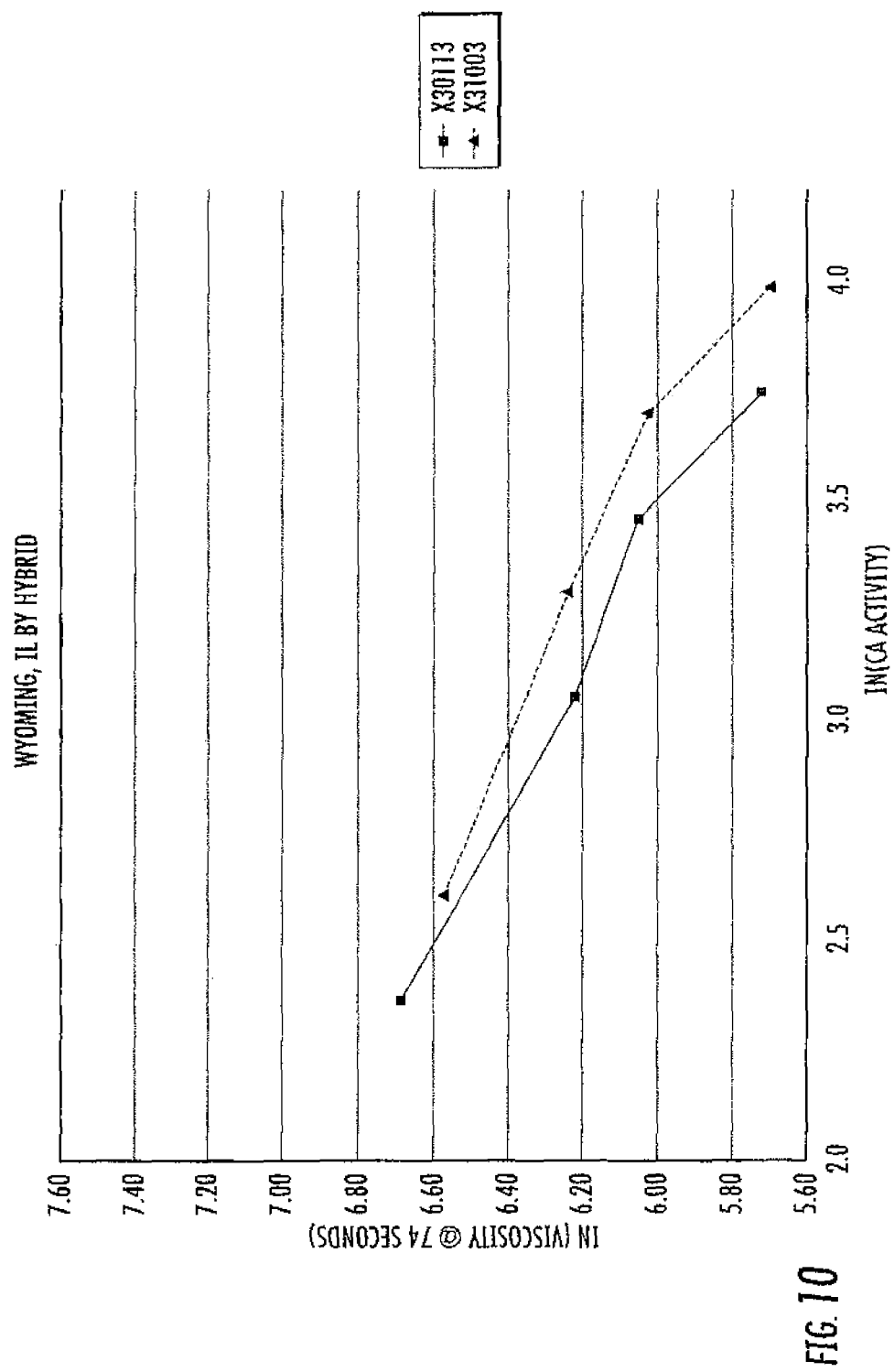
FIG. 10 shows viscosity changes between two corn hybrids (X50115 (squares) and X51005 (diamonds); n=4 for each hybrid) cultivated in Wyoming, Ill. (abscissa is the ln of CA activity; ordinate is the ln of viscosity at 74 seconds).

Results:

Standard curves were generated for each hybrid grown in various environments and conditions based on a correlation between viscosity and measured amylase activity as shown in FIGS. 3-10. Side-by-side comparison of standard curves indicate that one can distinguish hybrids and formulate a distinguishing database of standard curves to quickly identify unknown maize hybrids. As shown in FIG. 3, the assay distinguished corn hybrid X48005 from X50115. FIG. 4 shows that the assay distinguished corn hybrid X50115 from X51005. FIG. 5 shows that the assay distinguished corn hybrid X48005 from X50115. FIG. 6 shows that the assay distinguished corn hybrid X50115 and X51005. FIG. 7 shows that the assay distinguished corn hybrid X48005 from X50115. FIG. 8 shows that assay distinguished corn hybrid X50115 from X51005. FIG. 9 shows that the assay distinguished corn hybrid X48005 from X50115. FIG. 10 shows that the fast assay distinguished corn hybrid X50115 from X51005. In summary the assay reliably distinguished corn hybrid X48005 from X50115 and distinguished corn hybrid X50115 from X51005. Standard curves can be generated for maize plant hybrids of interest as described herein to generate a database of standard curves. If a plant is not engineered to express a alpha-amylase, one may use a commercial preparation of alpha-amylase and add to the slurry in incremental concentrations for example 10, 20, 30, and 40 U/g prior to the viscosity measurement. It is also envisioned that other starch or biomass degrading enzymes may be used to modulate changes in viscosity which be measured over a predetermined time for example glucoamylases and cellulases.

Example 4: Identification of Unknown Maize Hybrid by Comparing Against Standard Curves Standard Curves can be Generated for Maize Plant Hybrids of Interest as described in Example 1 to generate a database of standard curves.

If a plant is not engineered to express a alpha-amylase, one may use a commercial preparation of alpha-amylase and add to the slurry prior to viscosity measurement. It is also envisioned that other starch or biomass degrading enzymes may be used to modulate changes in viscosity which be measured over a predetermined time.

In order to identify an unknown maize hybrid expressing a thermophilic α-amylase the following methods may be used.

First, grinding seed of unknown hybrid (10-100 grams is sufficient) to a flour. Second, weigh approximately 9-20 grams of flour into a viscometer such as a Starchmaster® 2 Viscometer (Newport Scientific Pty. Ltd.; Warriewood, Australia). Third, mix flour with water to create a 28% dry solids corn slurry. Fourth, continue agitation via a gradual ramping up of the temperature to 95° C. (for example as shown in Table 1) measuring viscosity at 74 seconds. Fifth, measure amylase activity either by colorimetric methods (i.e. Amylazyme™ (Megazyme; Wicklow, Ireland)), or the methods as described in either Examples 1 or 2. Sixth, extrapolate 74 second viscosity data point and amylase activity onto database of known standard curves. Finally, identify unknown hybrid by matching data with standard curve of known maize hybrid located in said standard curve database.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method of distinguishing a first transgenic maize plant from a second maize plant, the method comprising the steps of:
    a. heating a solution of milled transgenic maize seed from a first transgenic maize plant comprising event 3272 expressing heterologous thermotolerant 797GL3 alpha-amylase enzyme to a temperature above a gelatinization temperature of starch, wherein the temperature is between about 60° C. to about 100° C.;
    b. continuously measuring viscosity changes of the solution for a time period of about 10 seconds to about 2 minutes, which results in only partial hydrolysis of starch;
    c. obtaining a viscosity curve for the first transgenic maize plant based on the measurements of step (b); and
    d. comparing the viscosity curve from the first transgenic maize plant to a viscosity curve obtained in the same manner from a second maize plant, wherein differences in the slopes of the viscosity curves distinguish the first transgenic maize plant from the second maize plant.

2. The method of claim 1, wherein the temperature is at least 80° C.

3. The method of claim 2, wherein the temperature is about 95° C.

4. The method of claim 1, wherein viscosity changes are measured from about 10 seconds to about 60 seconds.

5. The method of claim 1, wherein viscosity changes are measured at about 60 seconds.

6. The method of claim 1, wherein viscosity changes are measured at about 45 seconds.

7. The method of claim 1, wherein viscosity changes are measured at about 30 seconds.

8. The method of claim 1, wherein viscosity changes are measured at about 10 seconds.

9. A method of identifying a transgenic maize hybrid comprising event 3272 expressing a heterologous thermotolerant 797GL3 alpha-amylase enzyme, the method comprising the steps of:
    a. milling seed of the transgenic maize hybrid to create a flour;
    b. adding water to the flour, wherein the water results in a 10% to 50% dry solids corn slurry;
    c. heating the corn slurry of step b to a temperature above a gelatinization temperature of starch, wherein the temperature is between about 60° C. to about 100° C.;
    d. mixing the corn slurry of step c;
    e. continuously measuring viscosity of the corn slurry of step d at a time point between 10 seconds to 100 seconds, which results in only partial hydrolysis of starch;

f. measuring activity of the heterologous thermotolerant 797GL3 alpha-amylase;

g. extrapolating the viscosity data and activity data of steps c and f onto a database of standard curves, wherein the database of standard curves contains standard curves of known maize hybrids, and the standard curve of the maize hybrid is plotted in relation to alpha-amylase enzyme activity and viscosity at a time point between 10 seconds to 100 seconds; and h. comparing the standard curve of the maize hybrid to the standard curves of the known maize hybrids, wherein differences in the slopes of the standard curves can be used to identify the maize hybrid.

10. The method of claim 9, wherein viscosity changes are measured from about 10 seconds to about 60 seconds.

11. The method of claim 9, wherein viscosity changes are measured at about 60 seconds.

12. The method of claim 9, wherein viscosity changes are measured at about 45 seconds.

13. The method of claim 9, wherein viscosity changes are measured at about 30 seconds.

14. The method of claim 9, wherein viscosity changes are measured at about 10 seconds.

\* \* \* \* \*